(12) United States Patent
Sanati et al.

(10) Patent No.: US 11,850,386 B2
(45) Date of Patent: Dec. 26, 2023

(54) INFLATION DEVICES AND SYSTEMS FOR BALLOON CATHETERS AND METHODS FOR USE

(71) Applicant: Ostial Corporation, Campbell, CA (US)

(72) Inventors: Archimedes Sanati, Campbell, CA (US); Jake Wolenberg, Santa Clara, CA (US); Fred H. Co, Santa Clara, CA (US); Yi Yang, San Francisco, CA (US); Farhad Khosravi, Los Altos Hills, CA (US)

(73) Assignee: OSTIAL CORPORATION, Campbell, CA (US)

( * ) Notice: Subject to any disclaimer, the term of this patent is extended or adjusted under 35 U.S.C. 154(b) by 1003 days.

(21) Appl. No.: 16/592,739

(22) Filed: Oct. 3, 2019

(65) Prior Publication Data

US 2020/0108234 A1 Apr. 9, 2020

Related U.S. Application Data

(60) Provisional application No. 62/740,883, filed on Oct. 3, 2018.

(51) Int. Cl.
*A61M 25/10* (2013.01)
*A61F 2/958* (2013.01)
*A61M 29/02* (2006.01)

(52) U.S. Cl.
CPC ....... *A61M 25/10185* (2013.11); *A61F 2/958* (2013.01); *A61M 25/1011* (2013.01);
(Continued)

(58) Field of Classification Search
CPC .......... A61M 25/1011; A61M 25/1018; A61M 25/10184; A61M 25/10185;
(Continued)

(56) References Cited

U.S. PATENT DOCUMENTS 4,178,938 A 12/1979 Au
4,654,027 A * 3/1987 Dragan ........... A61M 25/10185
604/920

(Continued)

FOREIGN PATENT DOCUMENTS

WO WO 2017/125914 * 7/2017

OTHER PUBLICATIONS

Han, Inho, Korean Intellectual Property Office International Search Report and Written Opinion for corresponding International application No. PCT/US2019/054591, dated Feb. 28, 2020, 9 pages.

*Primary Examiner* — Sarah A Long
*Assistant Examiner* — Lindsey Bachman
(74) *Attorney, Agent, or Firm* — William A. English; Vista IP Law Group LLP

(57) ABSTRACT

Inflation devices and methods for using them are provided for selectively inflating and deflating multiple balloons on a catheter. For example, the inflation device may include a first valve including a plurality of first valve ports and a first valve member movable between multiple positions for opening and closing fluid paths between the first valve ports, a second valve including a plurality of second valve ports and a second valve member movable between multiple positions for opening and closing fluid paths between the second valve ports, and an actuator coupled to the first and second valve members for directing the first and second valve members between multiple positions, e.g., to selectively pull vacuum and sequentially inflate the balloons.

26 Claims, 14 Drawing Sheets

(52) U.S. Cl.
CPC ...... *A61M 25/10182* (2013.11); *A61M 29/02* (2013.01); *A61M 2025/1013* (2013.01)

(58) Field of Classification Search
CPC .. A61M 2025/1013; A61M 2025/1015; A61M 2025/1018
See application file for complete search history.

(56) References Cited

U.S. PATENT DOCUMENTS

| | | | |
|---|---|---|---|
| 5,725,535 A * | 3/1998 | Hegde | A61F 2/958 606/198 |
| 6,241,706 B1 * | 6/2001 | Leschinsky | A61M 60/497 604/99.01 |
| 6,419,657 B1 * | 7/2002 | Pacetti | A61F 2/958 604/920 |
| 7,582,111 B2 | 9/2009 | Krolik et al. | |
| 7,862,601 B2 | 1/2011 | Sanati et al. | |
| 8,486,134 B2 * | 7/2013 | Jablonski | A61M 25/1011 623/1.11 |
| 9,034,025 B2 | 5/2015 | Sanati et al. | |
| 2003/0078538 A1 | 4/2003 | Neale | |
| 2010/0298860 A1 * | 11/2010 | Thomas | A61M 25/1011 606/194 |
| 2012/0101515 A1 * | 4/2012 | Barbod | A61M 25/10187 606/194 |
| 2019/0063625 A1 * | 2/2019 | Liberman | F16K 27/003 |

* cited by examiner ially, simultaneously, and/or independently from one
INFLATION DEVICES AND SYSTEMS FOR BALLOON CATHETERS AND METHODS FOR USE The present application claims benefit of U.S. provisional application Ser. No. 62/740,883, filed Oct. 3, 2018, the entire disclosure of which is expressly incorporated by reference herein.

FIELD OF THE INVENTION

The present invention relates generally to devices and systems for inflating balloons on medical devices, and, more particularly, to devices, systems, and methods for inflating and/or deflating multiple balloons on catheters or other tubular devices during medical procedures, e.g., for flaring or otherwise expanding stents or other prostheses deployed within a body lumen, dilating stenoses, and the like.

BACKGROUND

Tubular endoprosthesis or "stents" have been suggested for dilating or otherwise treating stenoses, occlusions, and/or other lesions within a patient's vasculature or other body lumens. For example, a self-expanding stent may be maintained on a catheter in a contracted condition, e.g., by an overlying sheath or other constraint, and delivered into a target location, e.g., a stenosis within a blood vessel or other body lumen. When the stent is positioned at the target location, the constraint may be removed, whereupon the stent may automatically expand to dilate or otherwise line the vessel at the target location.

Alternatively, a balloon-expandable stent may be carried on a catheter, e.g., crimped or otherwise secured over a balloon, in a contracted condition. When the stent is positioned at the target location, the balloon may be inflated to expand the stent and dilate the vessel.

For some applications, catheters may be provided that include multiple balloons, e.g., side-by-side or at least partially overlapping balloons, that may be inflated sequentially, simultaneously, and/or independently from one another to expand a prosthesis in a desired manner, e.g., to deliver a stent at an ostium or bifurcation, i.e., where a branch vessel extends from a main vessel or trunk. Generally, using such a catheter may involve coupling multiple inflation devices, e.g., individual syringes, to separate ports of the catheter to allow inflation of the balloons independently of one another, which can complicate manipulation and use of the catheter.

Accordingly, devices and methods that facilitate inflating multiple balloons on catheters would be useful.

SUMMARY

The present invention is directed to devices and systems for inflating balloons on medical devices. More particularly, the present invention is directed to devices, systems, and methods for inflating and/or deflating multiple balloons on catheters or other tubular devices during medical procedures, e.g., for flaring or otherwise expanding prostheses deployed within a body lumen, dilating stenoses, and the like.

In accordance with an exemplary embodiment, an inflation device is provided for selectively inflating and deflating first and second balloons on a distal end of a tubular member via first and second lumens when the inflation device is coupled to a proximal end of the tubular device. The inflation device may include a first valve including a plurality of first valve ports and a first valve member movable between multiple positions for opening and closing fluid paths between the first valve ports, a second valve including a plurality of second valve ports and a second valve member movable between multiple positions for opening and closing fluid paths between the second valve ports, and an actuator coupled to the first and second valve members for directing the first and second valve members between multiple positions, e.g., sequentially between first, second, third, and fourth positions.

For example, with the first and second valve members in a first position, a fluid path is provided from a source of inflation media coupled to one of the first valve ports to the first and second lumens such that, the source of inflation media may be actuated to pull a vacuum along the fluid path to collapse the first and second balloons simultaneously. With the first and second valve members in a second position, the second lumen is isolated while a fluid path between the first lumen and the source of inflation media is open such that inflation media delivered from the source of inflation media through the first lumen inflates the first balloon. With the first and second valve members in a third position, the first lumen is isolated maintaining the first balloon inflated, and, with the first and second valve members in the fourth position, a fluid path from the source of inflation media to the second lumen is open while the first lumen remains isolated such that inflation media delivered from the source of inflation media through the second lumen inflates the second balloon.

In accordance with another embodiment, a method is provided for selectively inflating and deflating first and second balloons on a tubular member via first and second lumens. An inflation device may be provided that includes a first valve including a first valve port communicating with the first lumen, a second valve port communicating with a source of inflation media, a third valve port, and a first valve member movable between multiple positions for opening and closing fluid paths between two of the first, second, and third valve ports, and a second valve including a fourth valve port communicating with the third valve port, and a fifth valve port communicating with the second lumen, and a second valve member movable between multiple positions for opening and closing fluid paths between fourth and fifth valve ports. Optionally, the second valve may include a sixth valve port also communicating with the second lumen, e.g., in parallel with the fifth valve port. In this option, a flow restrictor and/or pressure relief device may be provided in line with the sixth valve port.

With the first and second valve members in a first position providing a fluid path from the source of inflation media to the first and second lumens, the source of inflation media may be actuated to pull a vacuum along the fluid path to collapse the first and second balloons simultaneously. The first and second valve members may then be directed to a second position isolating the second lumen while a fluid path between the first lumen and the source of inflation media is open and, with the first and second valve members in the second position, inflation media may be delivered from the source of inflation media through the first lumen to inflate the first balloon. The first and second valve members may then be directed to a third position isolating the first lumen, thereby maintaining the first balloon inflated. The first and second valve members may then be directed to a fourth position opening a fluid path from the source of inflation media to the second lumen while the first lumen remains isolated and, with the first and second actuators in the fourth position, inflation media may be delivered from the source of inflation media through the second lumen to inflate the second balloon. Optionally, the first and second valve members may be directed back to the first position to open a fluid path from the source of inflation media to the first and second lumens, and the source of inflation media may be actuated to pull a vacuum along the fluid path to collapse the first and second balloons simultaneously.

In accordance with yet another embodiment, an apparatus is provided for performing a medical procedure that includes a catheter and an inflation device for selectively inflating and deflating balloons on the catheter. For example, the catheter may include an elongate tubular member including a proximal end and a distal end sized for introduction into a patient's body; a first balloon on the distal end including a first interior communicating with a first lumen within the tubular member extending to a first lumen port on the proximal end; and a second balloon on the distal end including a second interior communicating with a second lumen within the tubular member extending to a second lumen port on the proximal end.

The inflation device may include a first valve including a first valve port communicating with the first lumen port, a second valve port communicating with a source of inflation media, a third valve port, and a first valve member movable between multiple positions for opening and closing fluid paths between the first, second, and third valve ports; a second valve including a fourth valve port communicating with the first valve port, a fifth valve port communicating with the second lumen port, and a second valve member movable between multiple positions for opening and closing fluid paths between fourth and fifth valve ports; and an actuator coupled to the first and second valve members for directing the first and second valve members between first, second, third, and fourth positions.

For example, with the first and second valve members in the first position, a fluid path is provided from the source of inflation media to the first and second lumens such that, the source of inflation media may be actuated to pull a vacuum along the fluid path to collapse the first and second balloons simultaneously. With the first and second valve members in the second position, the second lumen is isolated while a fluid path between the first lumen and the source of inflation media is open such that inflation media delivered from the source of inflation media through the first lumen inflates the first balloon. With the first and second valve members in the third position, the first lumen is isolated maintaining the first balloon inflated and, with the first and second valve members in the fourth position, a fluid path from the source of inflation media to the second lumen is open while the first lumen remains isolated such that inflation media delivered from the source of inflation media through the second lumen inflates the second balloon.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1A:
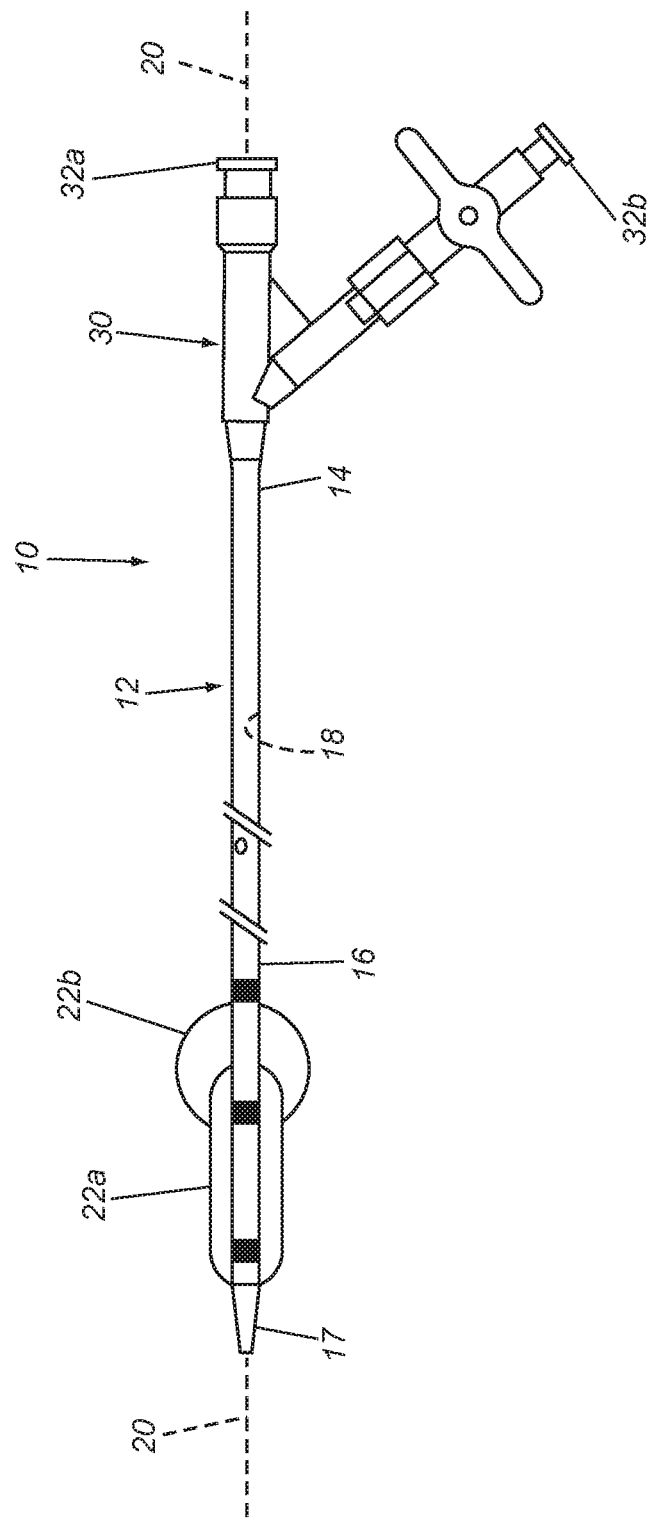
FIG. 1A is a side view of an exemplary embodiment of a catheter including multiple balloons for expanding a prosthesis or dilating a stenosis within a body lumen.

Before the exemplary embodiments are described, it is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Examples of inflation devices and systems are described herein that may be used with balloon catheters and/or other devices including multiple balloons that are introduced into a patient's body. Generally, the inflation devices may include adapters that may be integrated into a handle of a catheter or other tubular device, e.g., to achieve controlled inflation and/or deflation of multiple balloons via separate lumens of the tubular device, e.g., sequentially, simultaneously, and/or independently of one another. Alternatively, the components may be integrated into an external manifold that may include ports that may be coupled to respective ports, e.g., on a handle of a tubular device. Although separate embodiments are described below, it will be appreciated that components of the different embodiments may be combined with the other embodiments and/or multiples of each embodiment may be combined.

Figure 1B:
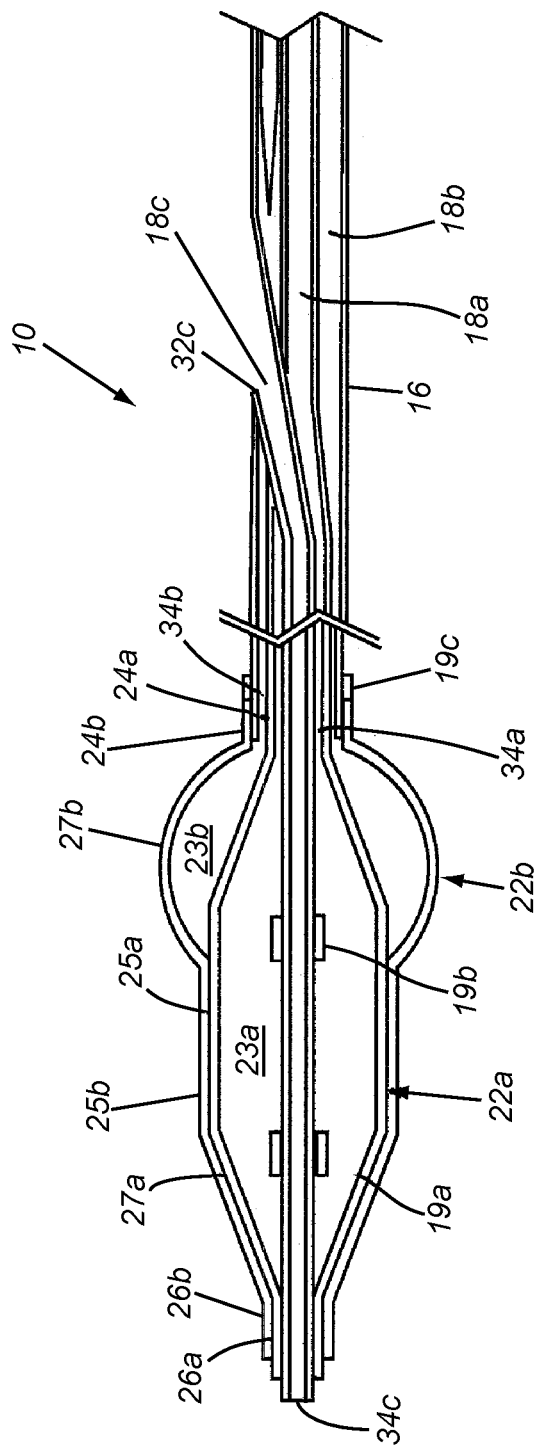
FIG. 1B is a cross-sectional detail of a distal end of the catheter of FIG. 1A with the balloons expanded.

Turning to the drawings, FIGS. 1A and 1B show an exemplary embodiment of a balloon catheter or apparatus 10 that may include any of the inflation devices or systems described herein, e.g., inflation device 110 (shown in FIGS. 2A-2D). Generally, the catheter 10 includes an elongate tubular member or body 12 having a proximal end 14, a distal end 16, and one or more lumens 18 extending between the proximal and distal ends 14, 16, thereby defining a longitudinal axis 20 extending between the proximal and distal ends 14, 16. Optionally, the catheter 10 may be provided as part of a kit or system including one or more additional components, such as external sources of inflation media, e.g., syringes, a guide catheter, and/or one or more guidewires (not shown).

As shown, the catheter 10 may include a pair of overlapping balloons or other expandable members 22 on the distal end 16, e.g., for flaring and/or otherwise expanding a stent previously deployed within a body lumen or carried on the distal end 16, for dilating a stenosis or valve, and/or for performing one or more other procedures within a patient's body (not shown), as described further elsewhere herein. In addition, the distal end 16 may include one or more markers, e.g., one or more bands of radiopaque material 19, to facilitate positioning the catheter 10 relative to a stent and/or anatomical structures within a patient's body. In addition or alternatively, the catheter 10 may include one or more therapeutic and/or diagnostic elements (not shown) on the distal end 16, e.g., within or carried by the balloon(s) 22, as described further below.

The tubular member 12 may be formed from one or more tubular bodies, e.g., having variable flexibility along its length. For example, the distal end 16 may be substantially flexible to facilitate introduction through tortuous anatomy, e.g., terminating in a rounded, tapered, and/or other substantially atraumatic distal tip 17. The distal end 16 may be sized and/or shaped for introduction into a body lumen, e.g., having a diameter between about one and seven millimeters (1-7 mm), or less than 1.7 millimeters. The proximal end 14 may be substantially flexible, semi-rigid, or rigid, e.g., having sufficient column strength to facilitate advancing the distal end 16 through a patient's vasculature by pushing on the proximal end 14. Optionally, a shaft support wire or other stiffener (not shown) may be provided within the proximal end 14, if desired, e.g., to facilitate pushing the catheter 10 from the proximal end 14. The tubular member 12 may be formed from plastic, metal, or composite materials, e.g., a plastic material having a wire, braid, or coil core, which may preventing kinking or buckling of the tubular member 12 during advancement.

As shown in FIG. 1A, the catheter 10 may include a handle or hub 30 on the proximal end 14, e.g., to facilitate manipulating the catheter 10. The handle 30 may include one or more ports 32 communicating with respective lumens 18 within the tubular member 12, as described further below, which may be coupled to corresponding ports on any of the inflation devices herein. Alternatively, at least some of the components of the inflation devices may be incorporated into the handle 30, e.g., one or more valves for opening and/or closing fluid paths from a source of inflation media to the lumens 18.

The handle 30 may be molded, machined, or otherwise formed from plastic, metal, or composite material, e.g., providing an outer casing, which may be contoured or otherwise shaped to ease manipulation. The proximal end 14 of the tubular member 12 may be attached to the handle 30, e.g., by bonding, cooperating connectors, interference fit, and the like. Optionally, if the catheter 10 includes any actuatable components (not shown) on the distal end 16, the handle 30 may include one or more actuators (also not shown), such as one or more slides, dials, buttons, and the like, for actuating or otherwise manipulating the components from the proximal end 14.

In the exemplary embodiment shown in FIG. 1B, the tubular member 12 includes at least three lumens 18 extending between the proximal and distal ends 14, 16. For example, the tubular member 12 may include inflation lumens 18a, 18b that extend from ports 32a, 32b in the handle 30 through the tubular member 12 to openings 34a, 34b and communicate within interiors 23a, 23b of respective balloons 22a, 22b. The ports 32a, 32b on the handle 30 may include connectors, e.g., a Luer lock connector (not shown), one or more seals (also not shown), and the like, to facilitate coupling an inflation device to the handle 30.

In addition, the tubular member 12 may include an instrument lumen 18c that extends from port 32c to an opening 34c in the distal tip 17. The instrument lumen 18c may have sufficient size to allow a guidewire or other rail or instrument (not shown) to be inserted therethrough, e.g., to facilitate advancing the catheter 10 over the rail, as explained further below. Alternatively, rather than a "rapid exchange" instrument lumen 18c, an instrument lumen (not shown) may be provided that extends from the handle 30 to the distal end 16. In this alternative, the handle 30 may include a port (not shown) and/or one or more seals (also not shown) that prevent fluid, e.g., blood, from flowing proximally out of the port, yet allow one or more instruments to be inserted therethrough and into the instrument lumen 18c.

Returning to FIGS. 1A and 1B, the tubular member 12 includes a first or inner balloon 22a and a second or outer balloon 22b on the distal end 16, which are expandable independently of one another. The balloons 22 may be bonded or otherwise secured to the distal end 16 of the tubular member 12, e.g., by bonding with adhesive, sonic welding, using an annular collar or sleeve, and the like. For example, as best seen in FIG. 1B, the inner balloon 22a may include a proximal end 24a attached directly to the distal end 16 of the tubular member 12 distal to instrument lumen port 32c and a distal end 26a attached directly to the distal end 16 adjacent the distal tip 17.

The outer balloon 22b includes a first or distal section 25b that extends at least partially over the inner balloon 22a and a second or proximal section 27b. For example, the first section 25b may extend entirely over the inner balloon 22a and a distal end 26b of the outer balloon 22b may be attached over or adjacent to the distal end 26a of the inner balloon 22a, e.g., by bonding, sonic welding, and the like, as described elsewhere herein. A proximal end 24b of the outer balloon 22b may be attached to the distal end 16 of the tubular member 12, e.g., proximal or adjacent to the inner balloon proximal end 24a and distal to the instrument lumen port 32c.

The first section 25b of the outer balloon 22b may overlie but remain separate from the underlying inner balloon 22a. Alternatively, the first section 25b may be bonded or otherwise attached to the inner balloon 22a, e.g., continuously or intermittently along the inner balloon 22a. Alternatively, the orientation of the outer balloon 22b may be reversed, if desired, e.g., with the second section 25b of the outer balloon 22b extending distally relative to the main section 25a of the inner balloon 22a rather than proximally. In a further alternative, a substantially spherical or bulbous section may be provided on the outer balloon 22b both proximally and distally to the main section 25a of the inner balloon 22a (not shown). In this alternative, the proximal and distal sections may be expanded simultaneously or independently of one another, as desired.

The inner balloon 22a may be expandable from a contracted condition (not shown) to an enlarged condition (shown in FIGS. 1A and 1B). Similarly, the outer balloon 22b may also be expandable from a contracted condition (not shown) to an enlarged condition (shown in FIGS. 1A and 1B). One or both balloons 22, e.g., inner balloon 22a, may be formed from substantially inelastic material, e.g., PET, nylon, or PEBAX, such that the balloon 22 expands to a predetermined size in its enlarged condition once sufficient fluid is introduced into the interior of the balloon 622. In addition or alternatively, one or both balloons 22, e.g., outer balloon 22b, may be formed from substantially elastic material, e.g., silicone, polyurethane, or polyethylene, such that the balloon 22 may be expanded to a variety of sizes depending upon the volume and/or pressure of fluid within the interior. In an exemplary embodiment, the inner balloon 22a may be formed from a semi-compliant or substantially non-compliant material, e.g., mid to high durometer PEBAX, nylon, or PET, and the outer balloon 22b may be formed from a substantially complaint or semi-compliant material, e.g., polyethylene, polyurethane, and low to mid durometer PEBAX.

To provide the proximal and distal sections 27b, 25b of the outer balloon 22b, the balloon material may be formed into a shape including a substantially spherical or other bulbous shape for the proximal section 27b and a substantially uniform, smaller diameter shape for the distal section 25b. For example, the balloon material may be blow molded within a mold having the desired shape for the outer balloon 22b when inflated. Because of the compliance of the balloon material, the outer balloon 22b, e.g., the proximal section 27b, may be expanded greater than the relaxed molded shape, yet may substantially maintain that shape unless constrained by external forces.

The outer balloon 22b may have a substantially uniform wall thickness, e.g., between the proximal and distal sections 27b, 25b. Alternatively, the wall thickness may vary; for example, the proximal section 27b may have a thinner wall thickness than the distal section 25b. Optionally, the outer balloon 22b may include one or more features thereon for enhancing traction, friction, or other engagement with structure contacted by the outer balloon 22b when expanded. For example, the outer surface of at least the proximal section 27b may be treated or textured, may include ribs or other protrusions, and the like (not shown) to increase friction or other engagement upon expansion.

In addition or alternatively, the balloons 22 may operate under different internal pressures and/or may require different pressures sufficient to fully expand the respective balloons 22. For example, the inner balloon 22a may require a greater inflation pressure to fully expand than the outer balloon 22b. This may allow the proximal section 27b of the outer balloon 22b to be expanded using a lower inflation pressure to flare and/or shape a flaring portion of a stent without substantial expansion of a main portion of the stent, as described further elsewhere herein and in the applications incorporated by reference herein.

Alternatively, during use, the outer balloon 22b may be inflated based upon delivering one or more predetermined volumes of fluid therein, e.g., in multiple stages of expansion, as described further below. For example, the proximal section 27b of the outer balloon 122a may be inflated upon delivering a first predetermined volume of fluid therein to flare the stent, e.g., between about 0.25-2 cubic centimeters or between about 0.5-4.2 cubic centimeters. Volume-based delivery may be useful for describing the function of the outer balloon 22b because of its relative compliance and/or low pressure requirements.

As shown in FIGS. 1A and 1B, the proximal section 27b of the outer balloon 22b may be shaped to expand to a substantially spherical shape in the enlarged condition, e.g., having a diameter between about ten and twenty millimeters (10-20 mm) when expanded using an inflation pressure between about one and five atmospheres (1-5 ATM). In an exemplary embodiment, the proximal section 27b of the outer balloon 22b may have a diameter of about thirteen millimeters (13 mm) at an inflation pressure of about two atmospheres (2 ATM). In contrast, the inner balloon 122b may be shaped to expand to a substantially cylindrical shape in the enlarged condition, e.g., having a diameter between about two and eight millimeters (2-8 mm) when expanded using an inflation pressure between about eight and twenty atmospheres (8-20 ATM).

In addition, a main section 25a of the inner balloon 22a may have a substantially uniform diameter, e.g., having a length between about eight and thirty millimeters (8-30 mm). Beyond the uniform diameter portion, the inner balloon 22a may have a transition portion 27a adjacent the distal tip 17. The transition portion 27a may be tapered, as shown, or may be substantially blunt, i.e., extending inwardly to the distal tip 17 (not shown). As shown, the main portion 25a of the inner balloon 22a may underlie at least a portion of the outer balloon 22b, e.g., the distal section 25b, as shown in FIG. 1B and as disclosed in the applications incorporated by reference elsewhere herein. In an exemplary embodiment, the main section 27a of the inner balloon 22a may have a diameter of between about five and six millimeters (5-6 mm) in the enlarged condition and may have a length of at least about seventeen millimeters (17 mm) distally beyond the proximal section 27b of the outer balloon 22b.

Additional information regarding balloon catheters or other tubular devices that may be used with the inflation devices and systems herein may be found in U.S. Pat. Nos. 7,862,601, 7,582,111, and 9,034,025, the entire disclosures of which are expressly incorporated by reference herein.

Turning to FIGS. 2A-2D, an exemplary embodiment of an inflation device 110 is shown that may be coupled to or integrated into a tubular device, such as the catheter 10 shown in FIGS. 1A and 1B. As shown, the inflation device 110 includes a pair of valves 112, 114, e.g., three-position stopcocks, coupled together via one or more passages 116, e.g., defined by one or more sections of tubing and the like. Each valve 112, 114 may include a valve body or cavity including a plurality of first valve ports and a valve member 112a, 114a movable within the valve body between multiple positions, e.g., for opening and closing a sequence of fluid paths between the valve ports and the catheter 10. For example, the valve members 112a, 114a may include one or more passages therethrough that may be aligned with one or more of the valve ports when the valve members 112a, 114a are rotated to one or more positions, as described elsewhere herein.

The valves 112, 114, and passages 116 may be contained with a rigid housing or manifold (not shown), which may be separate from the catheter 10. For example, the manifold may be shaped to be manipulated easily by a user during use, e.g., to actuate the valve members 112a, 114a and/or deliver vacuum or inflation media. In this embodiment, tubing may be connected between the housing and the handle 30, e.g., between the valves 112, 114 and ports 32a, 32b on the handle 30 for selectively delivering inflation media and/or vacuum to the lumens 18a, 18b and balloons 22a, 22b (not shown, see, e.g., FIG. 1B). Alternatively, the housing may be shaped or otherwise configured such that ports on the housing may be connected directly to the ports 32a, 32b on the handle 30. In addition, a source of inflation media, e.g., syringe 120, pump, and the like, may be connected to the housing, e.g., via tubing 122 such that the source 120 communicates with one of the valves, e.g., valve 112 to selectively deliver inflation media or vacuum to the fluid paths.

For example, the ports 32a, 32b and the housing of the inflation device 110 may include a pair of ports for connecting tubing between the inflation device 110 and handle 30 before use. The ports may include Luer fittings or other connectors to facilitate rapid connection and disconnection of the inflation device 110. Alternatively, tubing may be permanently connected to the housing that includes connectors for removably coupling the tubing to the ports 32a, 32b. Although shown as discrete valves, tubing, and connectors in FIGS. 2A-2D, components of the inflation device 110 may be integrally formed within the housing, e.g., by molding, casting, or otherwise creating passages corresponding to the indicated fluid paths.

In an alternative embodiment, the inflation device 110 may be integrated into the handle 30 of the catheter 10 (or other tubular device), e.g., such that the valve members are rotatably mounted within the handle 30 and tubing and/or passages within the handle shell define the fluid paths. In this alternative, the handle 30 may include only a single port, e.g., for connecting the syringe 120 or other source of inflation media to the inflation device integrated within the handle 30.

In addition, the inflation device 110 includes an actuator, e.g., a dial, slider, and the like (not shown), coupled to one or both of the valves 112, 114 for directing the valve members 112a, 114a between a plurality of positions, e.g., to open and/or close various valve ports and/or fluid paths, as described further below. In an exemplary embodiment, the actuator may be coupled directly to a first valve member 112a of the valve 112, and the other valve member 114b may be coupled to the first valve member such that actuation of the actuator causes the first valve member to rotate, thereby causing the second valve member to rotate.

Figure 2A:
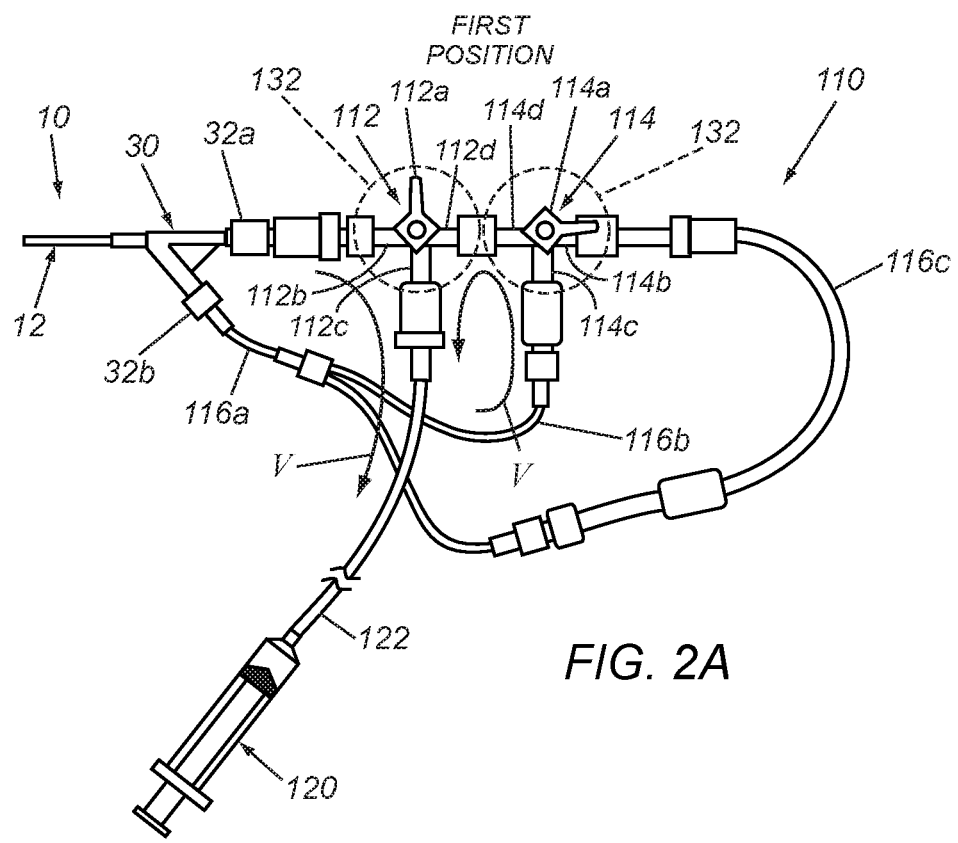
FIGS. 2A-2D are schematics showing an exemplary embodiment of an inflation device that may be coupled or integrated into a catheter handle including valves in different positions to control inflation and/or deflation of multiple balloons, such as the balloons on the catheter shown in FIGS. 1A and 1B.
Figure 2B:
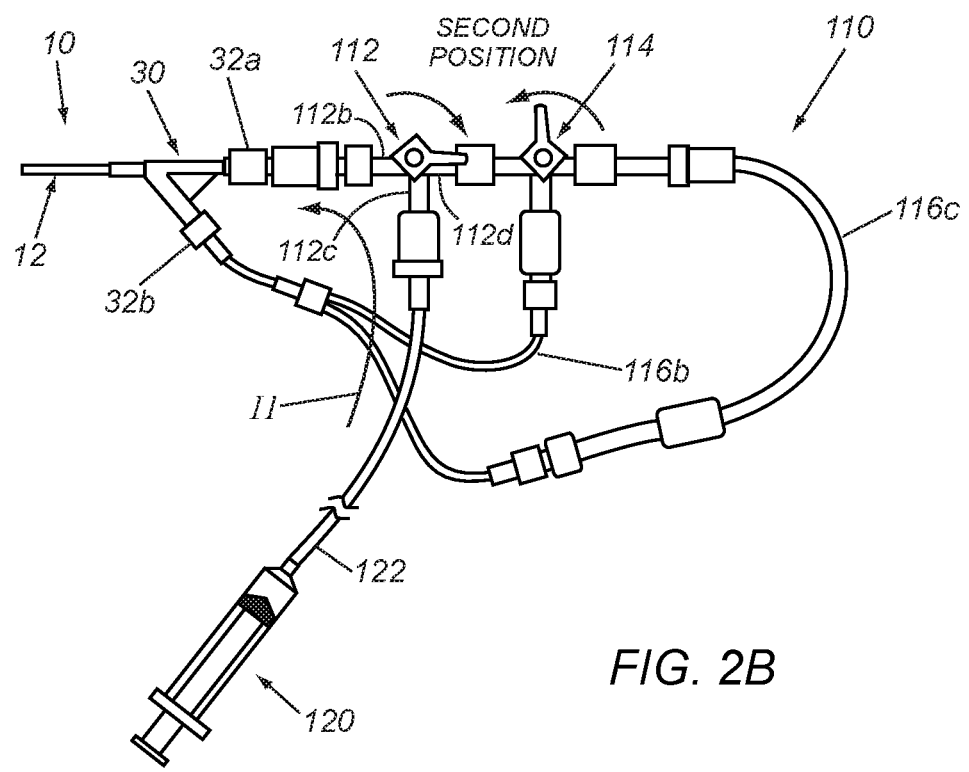
Figure 2C:
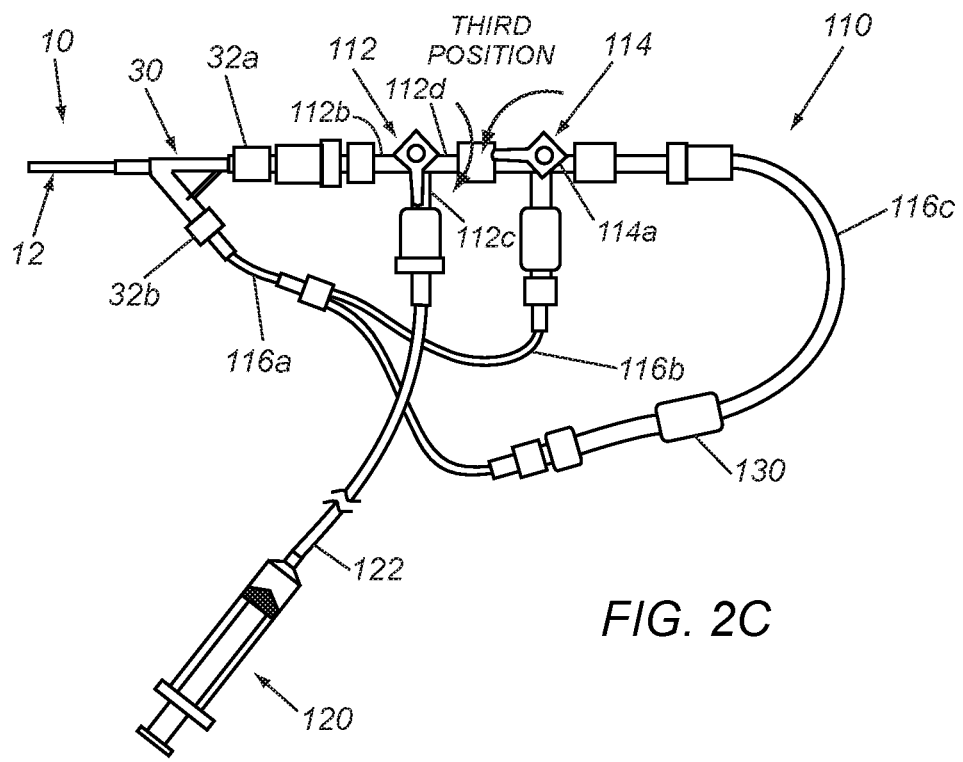
Figure 2D:
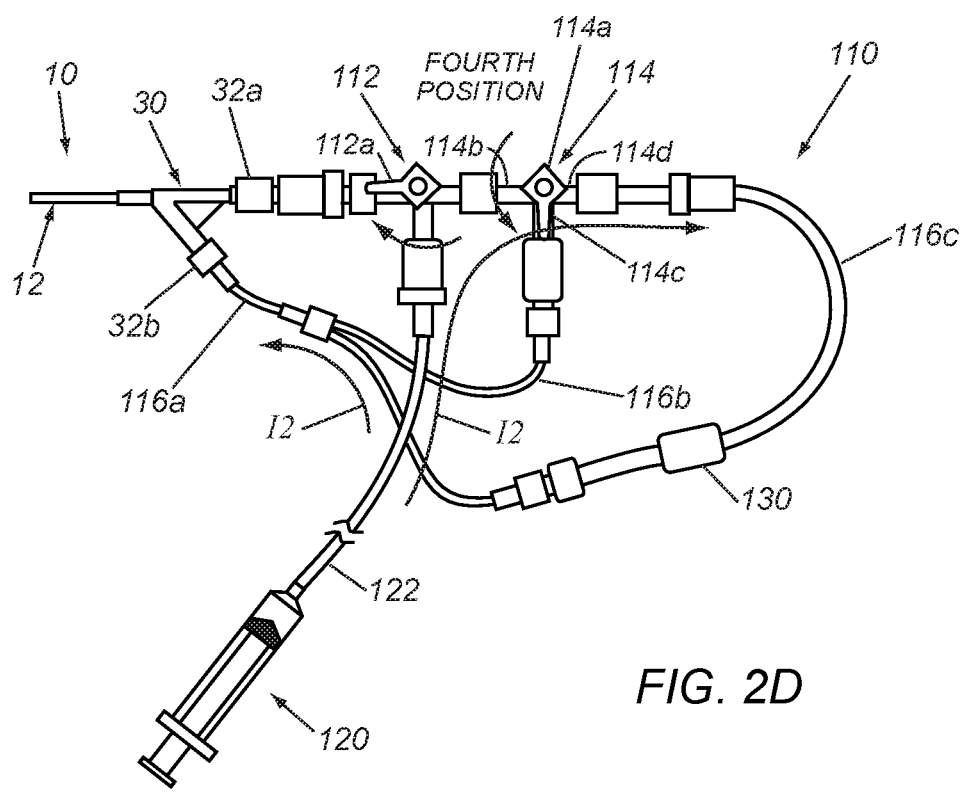

For example, as shown in FIG. 2A, the first and second valve members 112a, 114a may be rotatably coupled together by gears 132 (shown in phantom) such that rotation of the first valve member 112a in a clockwise direction causes the second valve member 114a to rotate in a counterclockwise direction, e.g., as indicated by the arrows in FIGS. 2B-2D. Consequently, rotation of the first valve member 112a, e.g., in a clockwise direction, by the actuator, may cause the second valve member 114a to rotate in an opposite direction, e.g., in a counterclockwise direction, to define a plurality of sequential positions, as indicated in FIGS. 2B-2D.

In the example shown, the actuator is rotatable in a first direction to direct the first and second valve members sequentially from a first position to second, third, and fourth positions, and eventually back to the first position. For example, the valve ports 112b, 112c, 112d and 114b, 114c, 114d may be offset about ninety degrees (90°) from one another around the valves 112, 114 such that the actuator may be manipulated to rotate the valve members 112a, 114a about ninety degrees between each sequential position, as shown in FIGS. 2A-2D. Alternatively, the actuator may be slidable axially or otherwise and may be coupled to one or both valve members 112a, 114a, e.g., by a rack and pinion or other arrangement (not shown), to cause the valve members 112a, 114 to rotate between the first-fourth positions when the actuator is slid axially (after which the actuator may be returned in the opposite direction back to the first position).

In the example shown in FIG. 2A, with the first and second valve members 112a, 114a in a first position, a fluid path is provided from the source of inflation media 120 to both ports 32a, 32b through the valves 112, 114 to the tubing 122 communicating with the syringe 120. Specifically, the first port 32a may communicate with a first valve port 112b of the first valve 112 and the valve member 112b may communicate with a second valve port 112c coupled to the tubing 122. Simultaneously, the second port 32b may communicate with the second valve 114a through tubing 116a, 116b, fifth valve port 114c and the second valve member 114a may communicate with a fourth valve port 114b coupled to a third valve port 112d of the first valve 112, which may communicate with the second valve port 112c and the tubing 122. Consequently, the syringe 120 may be actuated to pull a vacuum along the fluid paths, e.g., to generate a vacuum in both lumens 18a, 18b of the catheter 10 to collapse the first and second balloons 22a, 22b simultaneously, e.g., as indicated by arrows "V." For example, during preparation of the catheter 10, the balloons 22a, 22b may be collapsed to facilitate introduction into the patient's body and advancement to a target location, as described further below. In addition or alternatively, a source of fluid, e.g., saline may be coupled to the tubing 122 and used to flush the lumens 18a, 18b and/or balloons 22a, 22b simultaneously, before using the syringe 120 to pull a vacuum and collapse the balloons 22a, 22b.

Once the balloons 22a, 22b are positioned at a target location, e.g., after introducing the distal end 16 into a patient's body, as described further elsewhere herein, the actuator may be manipulated to direct the first and second valve members to a second position, e.g., as shown in FIG. 2B to isolate the third valve port 112d and consequently, close the fluid path through the second valve 114, the tubing 116b, 11a, and the port 32b such that the second lumen 18b is isolated. Simultaneously, a fluid path between the first lumen 18a and the syringe 120 is open, e.g., from the tubing 122, the second valve port 112c, the valve member 112a, the first valve port 112b, and the port 32a. Consequently, the syringe 120 may be advanced or otherwise manipulated to deliver inflation media from the syringe 120 along the fluid path, as indicated by arrow "I1" through the first 18a lumen to inflate the first balloon 22a.

After inflating the first balloon 22a, the actuator may be rotated or otherwise manipulated further to direct the first and second valve members 112a, 114a to the third position, e.g., as shown in FIG. 2C, to close the fluid path from the first valve member 112a through the first valve port 112b to the port 32a, thereby isolating the first lumen 18a and maintaining the first balloon 18a inflated.

Turning to FIG. 2D, the actuator may then be rotated further to direct the first and second valve members 112a, 114a to the fourth position, thereby opening a fluid path from the syringe 120 and tubing 122 through the fifth port 114c, the second valve member 114a, and the sixth port 114d, which communicates via tubing 116c, 116a to the port 32b. Consequently, while the first lumen 18a remains isolated (to keep the first balloon 22a inflated), inflation media may be delivered from the syringe 120 along the fluid path, as indicated by arrow "I2" through the second lumen 18b to inflate the second balloon 22b.

After inflating the second balloon 22b, the actuator may be rotated or otherwise manipulated back to the first position shown in FIG. 2A, thereby opening fluid paths from both lumens 18a, 18b to the syringe 120, which may then be actuated to pull a vacuum to collapse both balloons 22a, 22b simultaneously, whereupon the catheter 10 may be removed, e.g., as described further elsewhere herein.

Optionally, a flow restrictor 130 may be provided in one of the fluid paths, e.g., in line with tubing 116c such that flow along the fluid path with the actuator in the fourth position is limited in a desired manner. For example, if the second balloon 22b is an elastic and/or other low-pressure balloon, it may be desirable to limit flow of inflation media through the fluid path, i.e., through tubing 116c, 116a and the port 32a into the second lumen 18b, to prevent over-inflation of the second balloon 22b, which may risk rupturing the balloon 22b. Alternatively, if the first balloon 22a is an elastic and/or low-pressure balloon, a flow restrictor may be located in the fluid path between the first valve port 112b and the port 32a (not shown).

With particular reference to FIGS. 2D and 2A, it will be appreciated that, with the valve members 112a, 114a in the fourth position (FIG. 2D), inflation media may be delivered through tubing 116c (and the flow restrictor 130) into the tubing 116 and port 32b, while, with the valve members 112a, 114a rotated back to the first position (FIG. 2A), vacuum may be pulled through tubing 116b and 116a, i.e., bypassing the tubing 116c including the flow restrictor 130. Consequently, the second balloon 22b may be rapidly deflated without flow being limited by the flow restrictor 130. This advantage results from the parallel tubing lines 116b and 116c both communicating from the second valve 114 to the tubing 116a and port 32b.

Optionally, before directing the actuator from the fourth position back to the first position, the syringe 120 may be manipulated to pull vacuum to at least partially collapse the second balloon 22b. For example, if the first balloon 22a is an inelastic and/or other high-pressure balloon, when the actuator is moved to the first position, pressure from the first balloon 22a may travel through the first lumen 18a into the fluid paths of the inflation device 110 and expose the fluid path to the second lumen 18b and second balloon 22b to this pressure, which may otherwise risk over-inflation of the second balloon 22b.

In addition or alternatively, a pressure relief valve or device (not shown) may be provided in one or more of the fluid paths to limit pressure within the fluid path to a predetermined maximum pressure. For example, if the second balloon 22b is an elastic and/or other low pressure balloon, a pressure relief valve may be provided in the fluid path communicating with the port 32b, e.g., in line with tubing 116c similar to the flow restrictor 130. Such a pressure relief valve may prevent over-inflation of the second balloon 22b, e.g., as described further elsewhere herein.

Turning to FIGS. 3A-3F, an exemplary method is shown for using the catheter 10 to flare and/or otherwise expand a stent 40 deployed within a patient's body, e.g., including an ostium 90. As shown, the ostium 90 may be an opening in a wall of a first or main body lumen or trunk 92 that communicates with a second body lumen or branch 94. In exemplary embodiments, the main body lumen 92 may be the ascending or descending aorta, and the branch body lumen may be a coronary artery, a common carotid artery, or a peripheral artery. A stenosis, occlusion, or other lesion 96 may exist at and/or adjacent to the ostium 90, e.g., extending at least partially into the branch 94. The lesion 96 may include atherosclerotic plaque or other material that partially or completely occludes blood or other fluid flow between the trunk 92 and the branch 94.

Figure 3A:
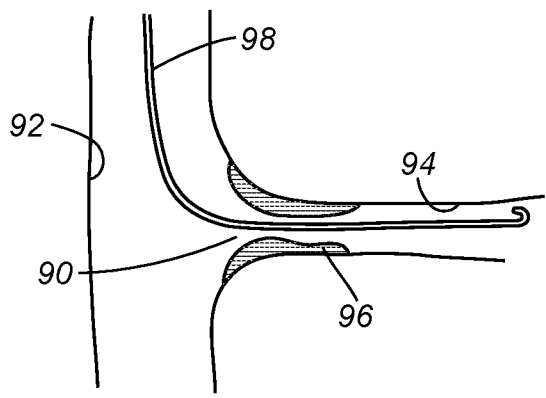
FIGS. 3A-3F are cross-sectional views of a patient's body including an ostium communicating between a main vessel and a branch vessel, showing a method for flaring a stent previously deployed within the branch vessel using the catheter of FIGS. 1A and 1B.
Figure 3B:
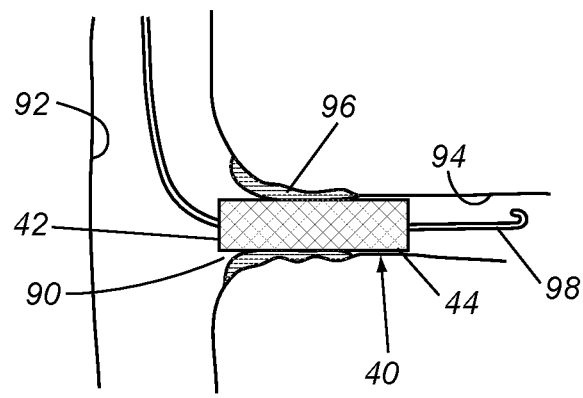

Initially, as shown in FIG. 3A, a guidewire 98 or other rail may be introduced from the trunk 92 through the ostium 90 into the branch 94, e.g., using conventional methods. For example, a percutaneous puncture or cut-down may be created at a peripheral location (not shown), such as a femoral artery, carotid artery, or other entry site, and the guidewire 98 may be advanced through the patient's vasculature from the entry site, e.g., alone or with the aid of a guide catheter (not shown). For example, a distal end of a guide catheter (not shown) may be advanced over the guidewire 98 into the trunk 92, e.g., until the distal end is disposed adjacent or proximal to the ostium 90. The guide catheter may be used to advance one or more instruments (such as any of the catheters or other devices described herein) over the guidewire 98 and into the trunk 92 and/or branch 94.

If the lesion 96 completely occludes the branch 94, the guidewire 98 may be directed through the occlusion, or other devices (not shown) may be advanced over the guidewire 98 or otherwise in conjunction with the guidewire 98 to create a passage through the lesion 96 for the guidewire 98.

After the guidewire 98 is directed into the branch 94 beyond the lesion 96, it may be desirable to at least partially dilate the lesion 96. For example, an angioplasty catheter (not shown) may be advanced through the guide catheter and/or over the guidewire 98 into and through the lesion 96, whereupon a balloon or other element on the catheter may be expanded to at least partially dilate the lesion 96. If desired, other procedures may also be performed at the lesion 96, e.g., to soften, remove, or otherwise treat plaque or other material forming the lesion 96, before the stent 40 is implanted. After completing any such procedures, any instruments advanced over the guidewire 98 may be removed.

To deliver the stent 40, any delivery catheter and/or conventional procedure may be used. For example, a distal end of a delivery catheter (not shown) may be advanced over the guidewire 98 and/or through the guide catheter from the entry site into the trunk 92. For example, with the distal end of the guide catheter against or adjacent the ostium 90, the distal end of the delivery catheter may be advanced from the guide catheter, through the ostium 90, and into the branch 94. The delivery catheter may be positioned such that the stent 40 extends into and through the lesion 96 and/or branch 94. The stent 40 may be expanded and/or otherwise deployed from the delivery catheter to place the stent 40 across the lesion 96 and/or within the branch 94. For example, as shown in FIG. 2B, the stent 40 may be deployed such that a first end 42 of the stent 40 extends at least partially into the ostium 90 and/or the trunk 92, and a second end 44 of the stent 40 is disposed within the branch 94 beyond the lesion 96.

As shown, the stent 40 may have a substantially uniform diameter cross-section once deployed. For example, the stent 40 may be expanded to dilate and/or otherwise engage the lesion 96 and/or branch 94. Alternatively, the stent 40 may be partially expanded using the delivery catheter, allowing the stent 40 to be further expanded by the apparatus 10, as described below.

Figure 3C:
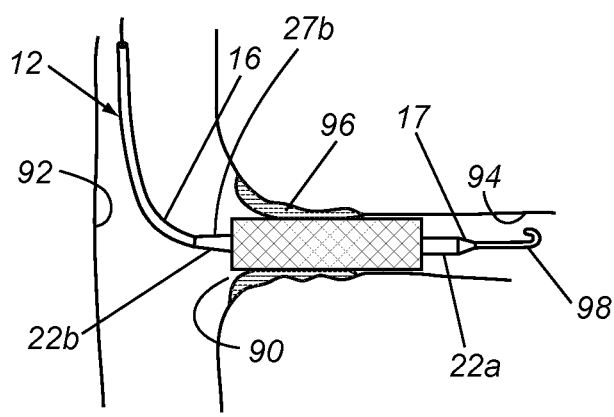

Turning to FIG. 3C, thereafter, the distal end 16 of the catheter 10 (with the balloons 22 in their contracted conditions) may be introduced into the trunk 92 to flare and/or otherwise expand the stent 40. Before introduction, the actuator may be manipulated to direct the valve members 112a, 114a to the first position shown in FIG. 2A, whereupon a vacuum may be applied via the syringe 120 to simultaneously collapse and/or otherwise prepare the balloons 22 for introduction.

For example, the delivery catheter may be removed, and the distal end 16 of the catheter 10 may be advanced over the same guidewire 98 into the trunk 92. In the embodiment shown in FIG. 1B, a proximal end (not shown) of the guidewire 98 may be backloaded into the opening 34c through the instrument lumen 18c and out the port 32c. The distal end 16 may then be advanced over the guidewire 98 into the patient's body over the guidewire 98.

As shown in FIG. 3C, the distal end 16 may be advanced through the stent 40 and ostium 90 at least partially into the branch 94. For example, the distal end 16 may be positioned such that the inner balloon 22a is positioned within and/or beyond the stent 40, e.g., beyond the first end 42, and the proximal section 27b of the outer balloon 22b is positioned adjacent the ostium 90, e.g., within and/or proximal to the first end 42 of the stent.

Optionally, to facilitate positioning, the distal end 16 may be monitored using fluoroscopy or other external imaging, e.g., to observe and monitor markers 19 (not shown, see FIG. 1B) on the distal end 16. For example, markers 19a and 19b may be located on the distal end 16 to identify the ends of the substantially uniform main section 25a of the inner balloon 22a, while proximal marker 19c may be located on the distal end 16 to identify the proximal end 24b and/or proximal section 27b of the outer balloon 22b. Thus, with the markers 19, the inner balloon 22a may be aligned with the distal end 44 and/or portion of the stent 40 within the branch 94 beyond the ostium 90 and the proximal section 27b of the outer balloon 22b may be aligned with the first end 42 of the stent 40 and/or the ostium 90, as desired.

Figure 3D:
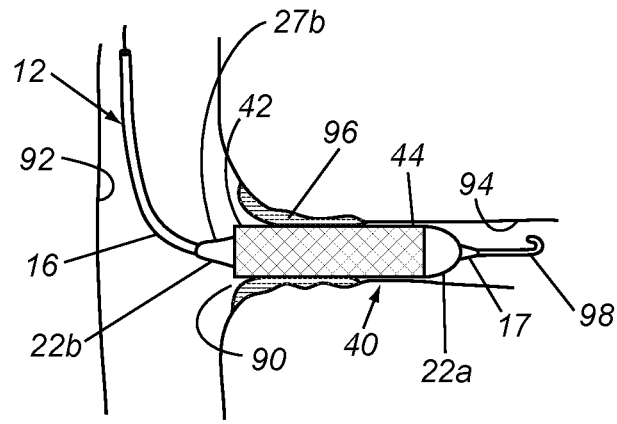

Turning to FIG. 3D, with the distal end 16 positioned as desired, the inflation device 110 may be operated to inflate the balloons 22 in a desired manner to flare and/or otherwise further expand the stent 40. For example, the actuator may be directed to the second position shown in FIG. 2B, whereupon the inner balloon 22a may be expanded to engage the stent 40 and/or wall of the branch 94, e.g., expanded to engage both the second end 44 of the stent 40 and the wall of the branch 94 beyond the stent 40 to prevent substantial axial migration of the stent 40.

Figure 3E:
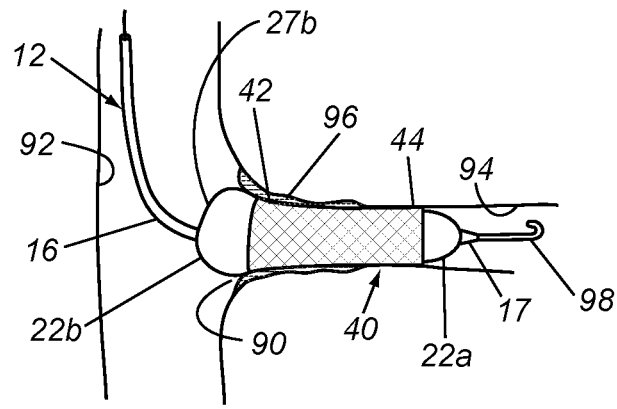
Figure 3F:
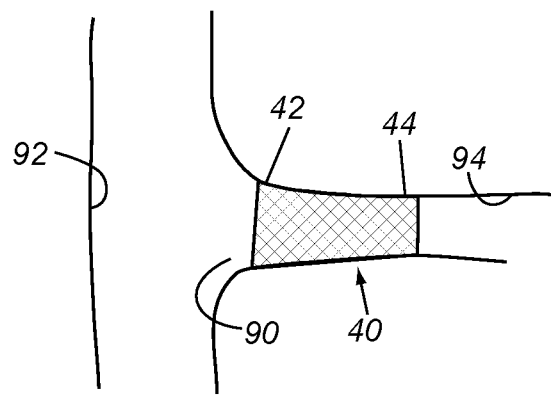

Thereafter, the actuator may be directed to the third position to isolate the inner balloon 22a and keep the balloon 22a inflated, as shown in FIG. 2C. The actuator may then be directed to the fourth position, as shown in FIG. 2D and the proximal section 27b of the outer balloon 22b may be expanded to flare the stent 40, e.g., as shown in FIG. 3E. For example, as the proximal section 27b is expanded, the first end 42 of the stent 40 is expanded, e.g., into a flared configuration, which may conform to the shape of the proximal section 27b and/or the ostium 90. With the inner balloon 22a expanded, the stent 40 and distal end 16 may remain substantially stationary during this inflation and flaring.

Optionally, after inflating the proximal section 27b and flaring the first end 42 of the stent 40, the inner balloon 22a may be inflated further, if desired, e.g., to expand the stent 40 and further dilate the lesion 96. With the stent 40 fully deployed, the actuator may be directed to the first position shown in FIG. 2A, and the balloons 22 may be deflated or otherwise collapsed, e.g., simultaneously. The catheter 10 may then be withdrawn from the branch 94 and trunk 92, and from the patient's body, e.g., into the guide catheter (not shown). The guide catheter and/or guidewire 98 may then be removed from the patient's body, leaving the stent 40 in place, as shown in FIG. 2F.

In alternative embodiments, other inflation sequences may be used with the inflation devices herein, e.g., to initially deliver and deploy a stent and then flare the stent, e.g., within an ostium 90. In still another alternative, the catheter 10 may be used to expand a stent previously placed within a substantially straight or other non-bifurcated body lumen, such as within a carotid, iliac, renal, coronary artery, or other blood vessel. In a further alternative, a stent or other prosthesis, such as those disclosed in the applications incorporated by reference herein, may be provided on the distal end 16 of the catheter 10, e.g., over the balloons 22, rather than on a separate delivery catheter, if desired.

Turning to FIGS. 4A-4D, another example of an inflation device 210 is shown that includes a flow control manifold 212 communicating with ports 32a, 32b on a handle 30 of a catheter 10 and a syringe or other source of inflation media 120, e.g., via tubing 216, generally similar to the previous embodiments. An actuator may be coupled to one or more valve members of the manifold 212 (not shown), e.g., for opening and closing ports 212a, 212b, 212c of the manifold 212. in a desired manner to facilitate applying vacuum and/or delivering inflation media to the ports 32a, 32b to collapse and/or expand balloons (not shown) on the catheter 10. For example, the manifold 212 may include two valves therein with valve ports arranged to provide one or more fluid paths, similar to other embodiments herein.

Figure 4A:
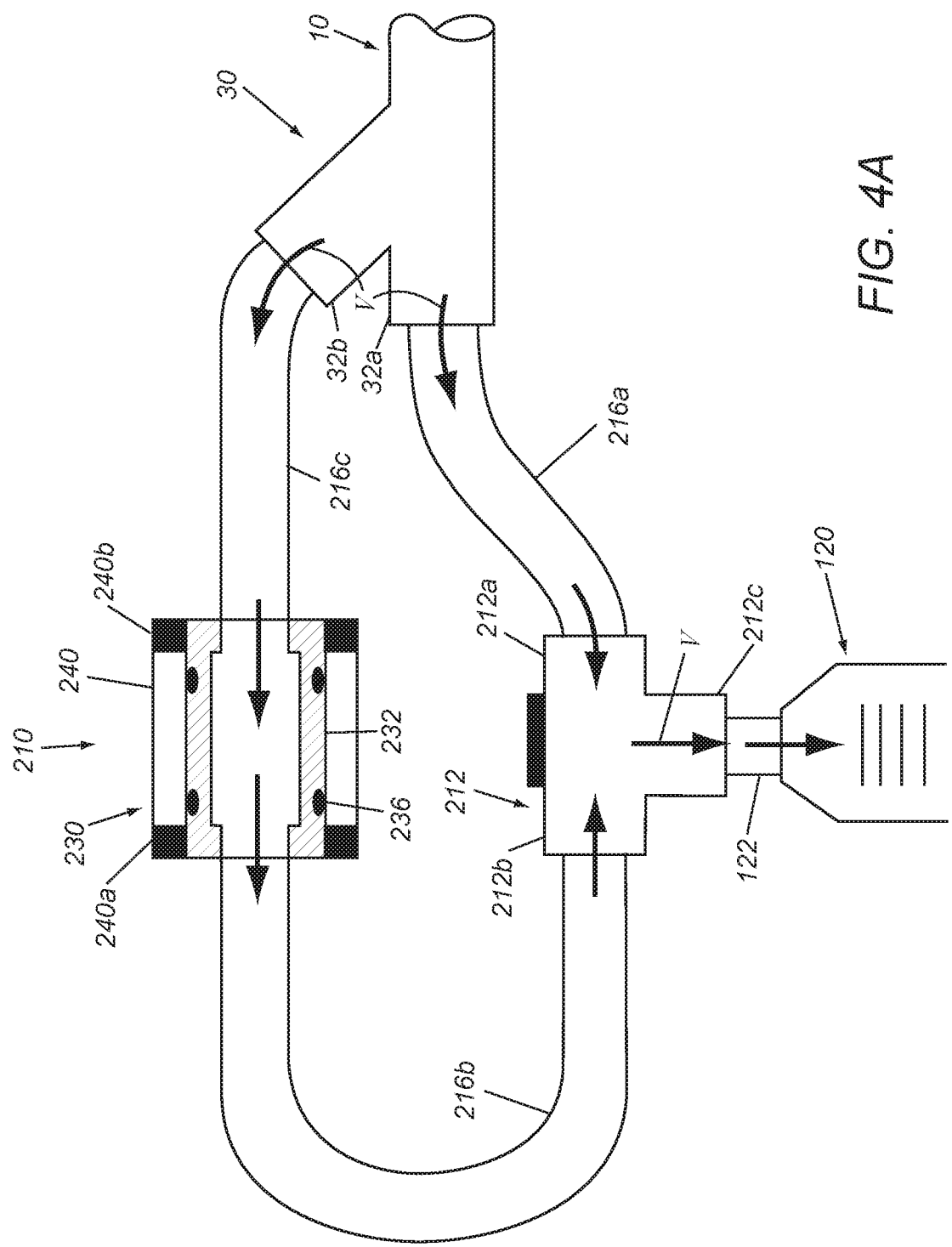
FIGS. 4A-4D are schematics showing another exemplary embodiment of an inflation device including a pressure relief valve.

For example, in a first position, shown in FIG. 4A, both ports 32a, 32b communicate with the syringe 120 via tubing 216 and open ports 212a, 212b, 212c of the manifold 212. Consequently, the syringe 120 may be manipulated to draw vacuum through the inflation device 210, as indicated by arrows "V" through both fluid paths including tubing 216a, 216b/216c to collapse both balloons simultaneously.

Figure 4B:
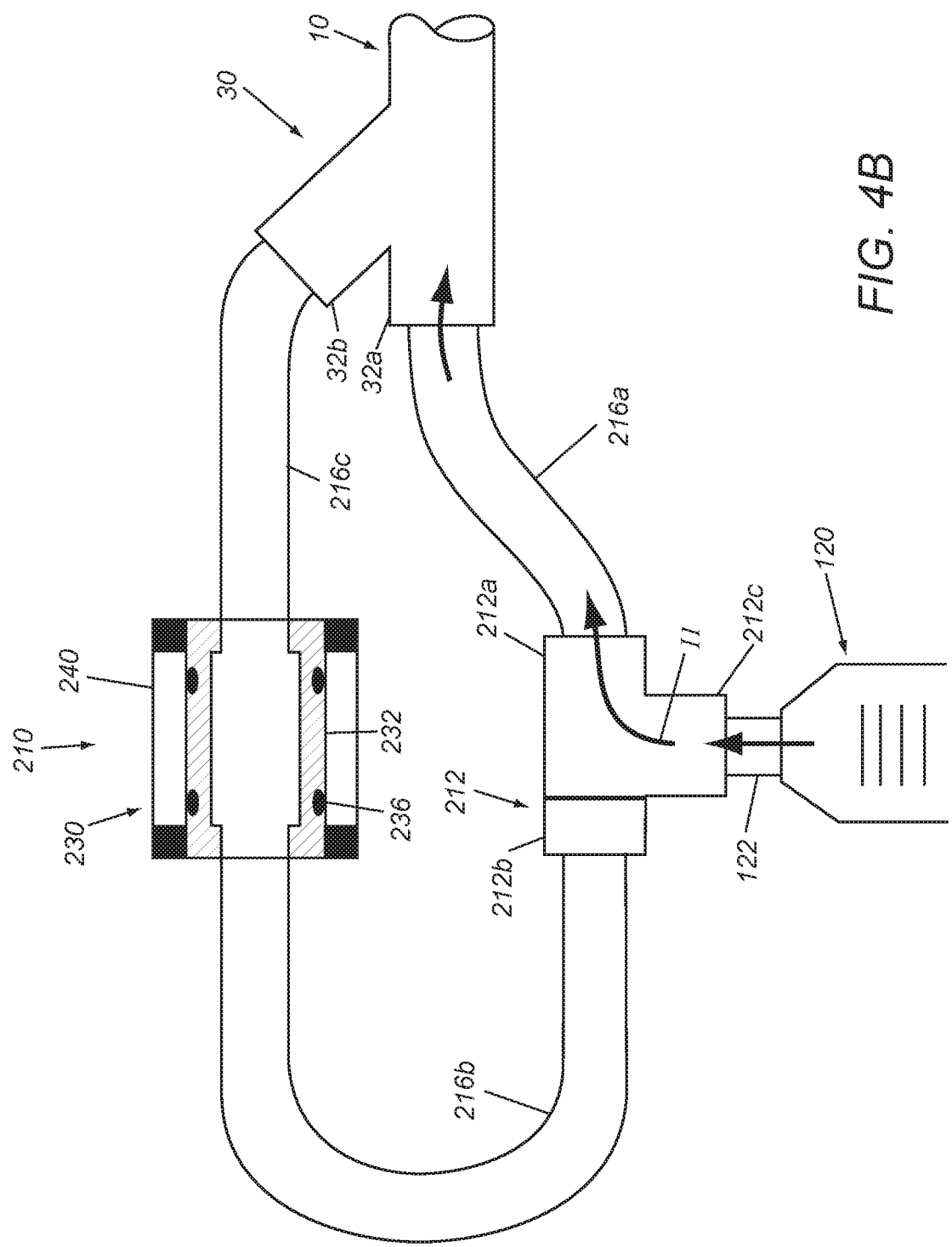

In a second position, shown in FIG. 4B, the actuator has been directed to close the second manifold port 212b communicating via tubing 216b, 216c to the second port 32b while the first manifold port 212a remains open and in communication the third manifold port 212c. Consequently, the syringe 120 may be manipulated to deliver inflation media though the manifold 212 and tubing 216a to the first port 32a for inflating the first balloon while the second balloon remains collapsed (not shown, see, e.g., FIG. 3D).

Figure 4C:
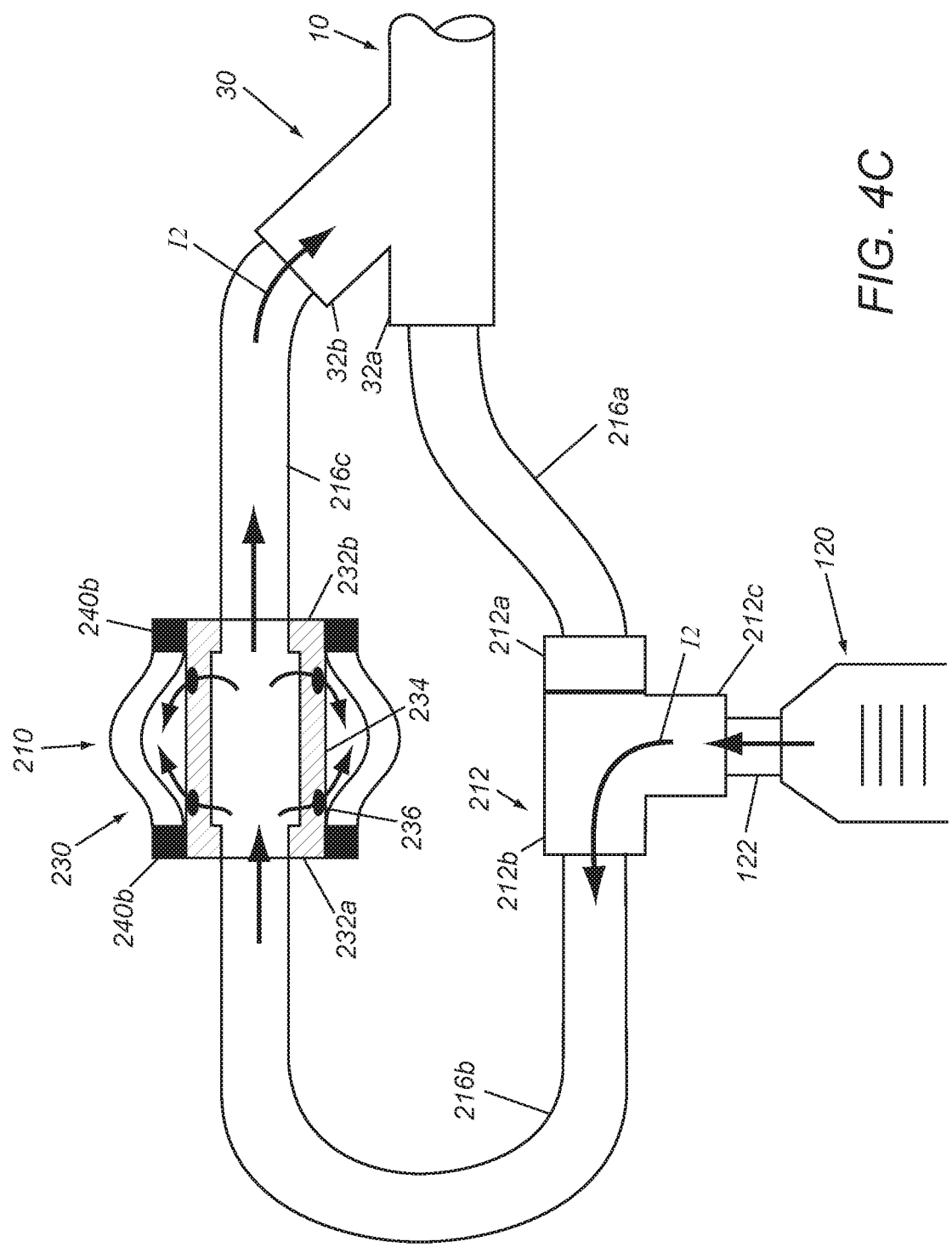

In a third position, shown in FIG. 4C, the actuator has been directed to open the second manifold port 212b and close the first manifold port 212a, thereby opening a fluid path via tubing 216b, 16c to the second port 32b. Consequently, the syringe 120 may be manipulated to deliver inflation media though the manifold 212 and tubing 216b, 216c to the second port 32b for inflating the second balloon while the first balloon remains inflated (not shown, see, e.g., FIG. 3E).

As shown, a pressure relief valve 230 is provided in line with the tubing 216b, 216c to limit the pressure of inflation media delivered to the second port 32b and, consequently, the second balloon 22b (shown in FIG. 1B). For example, as described above, the second balloon 22b may be an elastic and/or low-pressure balloon and so, it may be desirable to limit pressure delivered into the balloon 22b to avoid over-inflation and/or rupture.

To accomplish this, the pressure relief valve 230 includes a substantially rigid casing or housing 232 including ends 232a, 232b with ports for communicating with the tubing 216b, 216c and a sidewall 234 including one or more holes 236. The valve 230 also includes a flexible piece of tubing, bladder, or other material 240 mounted around an outer surface of the casing 232, e.g., including ends 240a, 24b attached to the ends 232a, 232b of the casing 232 to provide an enclosed and/or sealed interior region communicating with the hole(s) 236. The hole(s) 236 permit inflation media entering the casing 232 to escape therethrough to expand the bladder 240 when a predetermined pressure is exceeded.

For example, when the manifold 212 is in the third position, shown in FIG. 4C, excess pressure may cause the bladder 240 to expand thereby storing excess inflation media within bladder 240 and preventing the excess pressure from passing through to the second port 32b and the interior of the second balloon 22b. If the pressure of the inflation media falls below the predetermined pressure, the bladder 240 may be biased to collapse towards the casing 232, thereby directing the excess inflation media out of the casing 232, e.g., along tubing 216c into the second port 32b. Thus, the pressure relief valve 230 may facilitate maintaining the second balloon 22b at a desired inflation pressure when inflated even if the pressure from the syringe 120 varies.

The bladder 240 may be formed from semi-compliant or compliant material, e.g., having desired wall thickness, durometer, length, and/or other mechanical properties, to set the predetermined pressure at a target maximum pressure. In addition, the number and/or size of holes 236 may be selected to adjust the predetermined pressure.

Figure 4D:
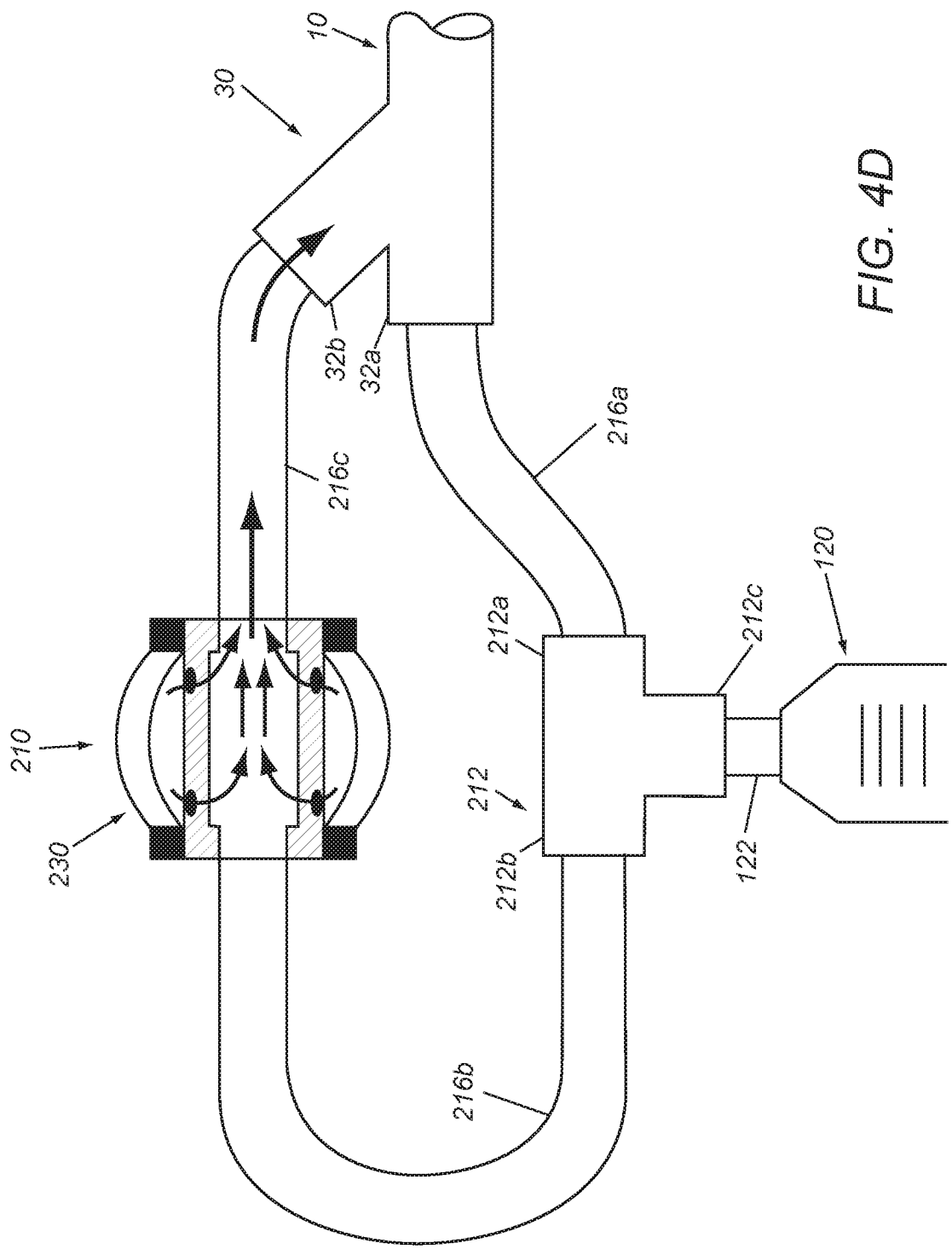
Figure 5A:
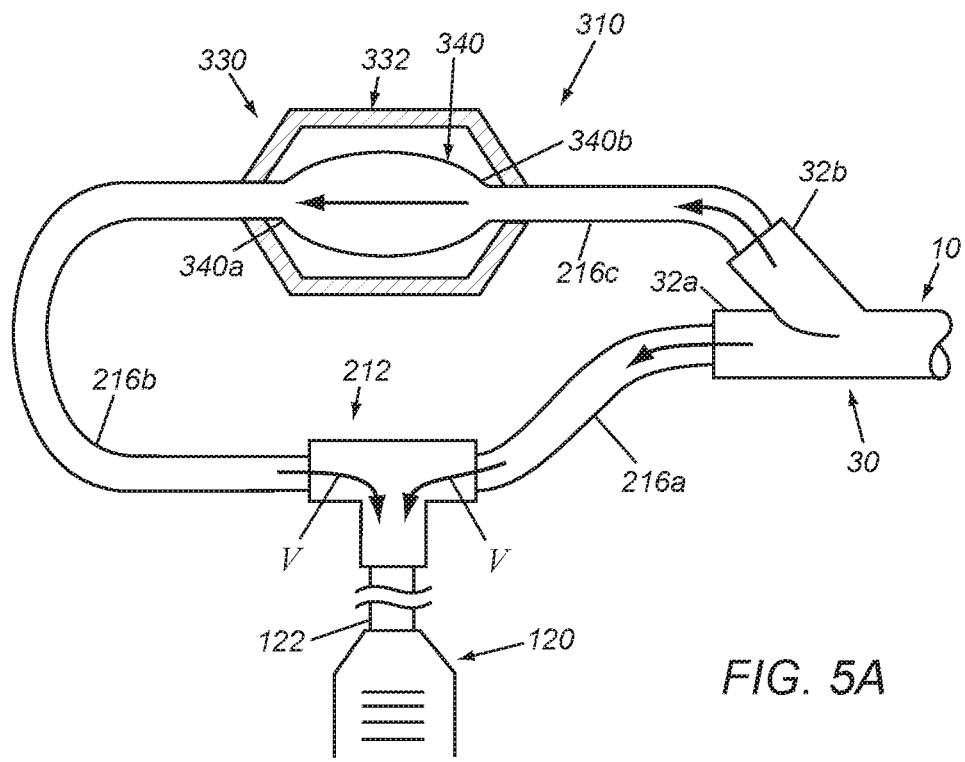
FIGS. 5A-5D are schematics showing yet another exemplary embodiment of an inflation device including a pressure relief valve.
Figure 5B:
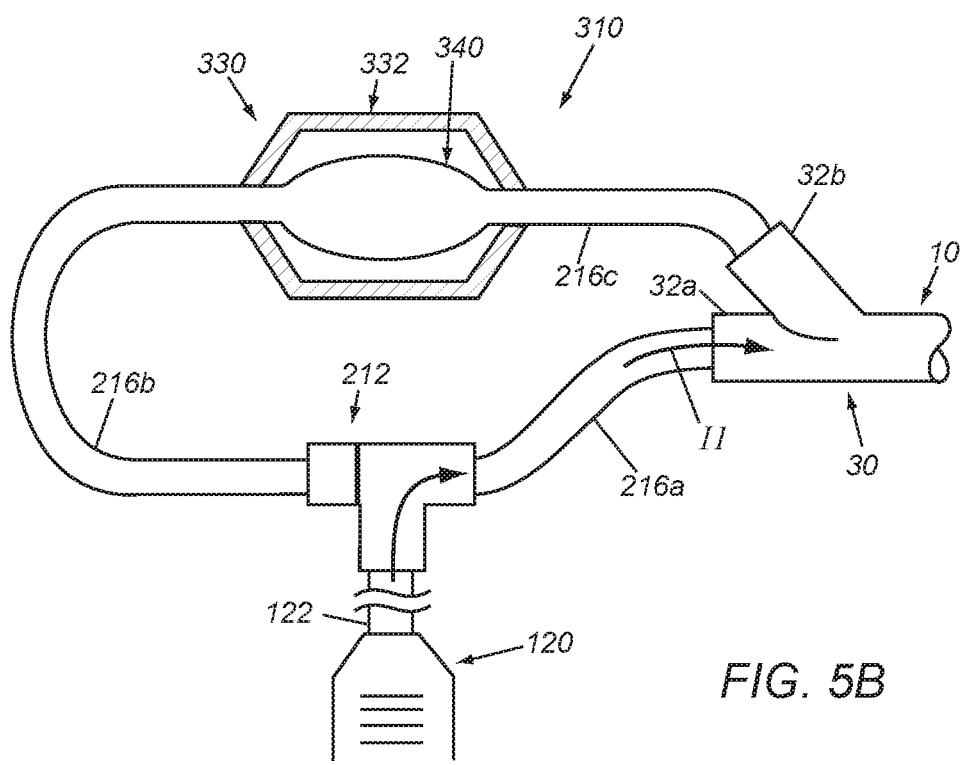
Figure 5C:
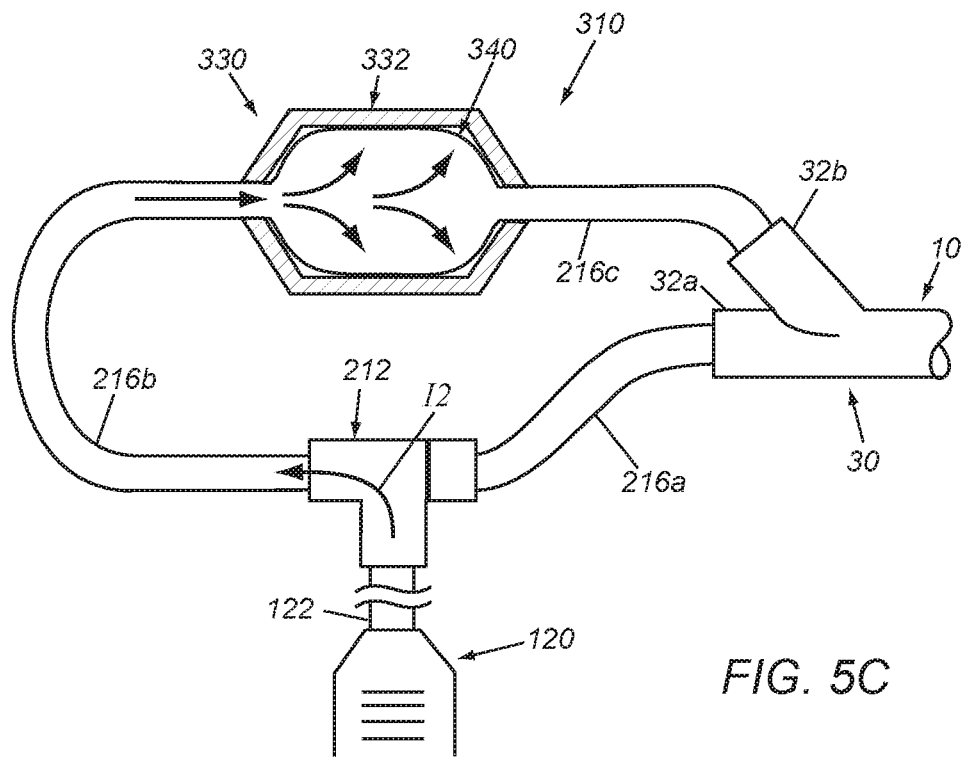
Figure 5D:
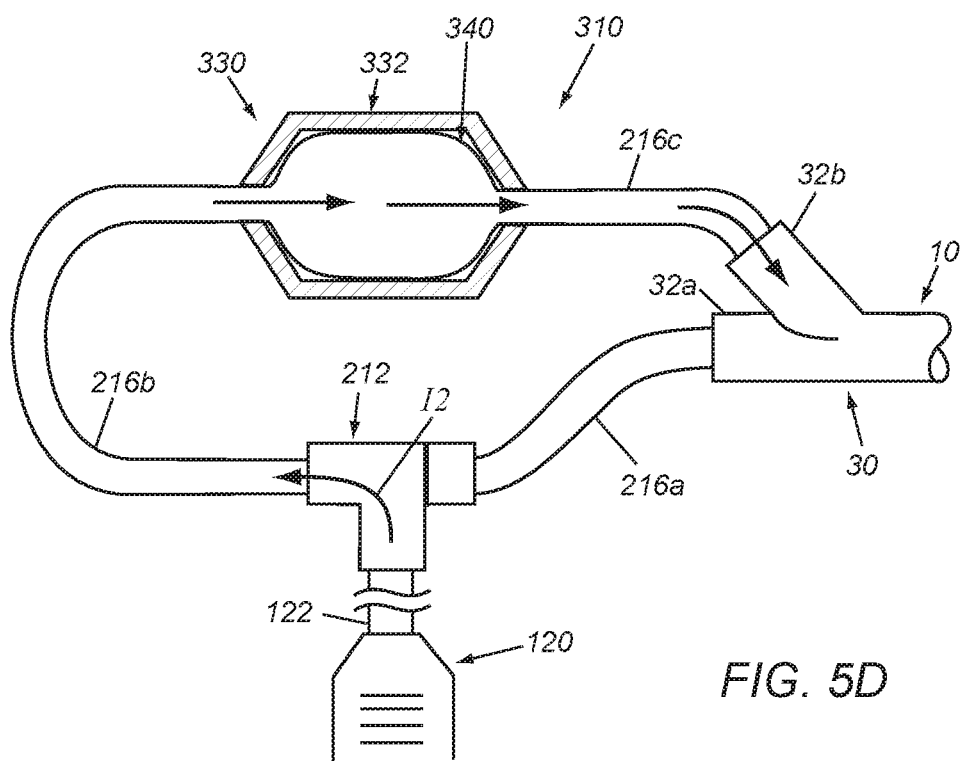

When the manifold 212 is directed from the third position to the fourth position, shown in FIG. 4D, the pressure relief valve 230 may prevent excessive pressure from being applied to the second port 32b and, consequently, the second balloon 22b. Thus, the pressure relief valve 230 may store a volume of inflation media and/or store a target pressure within the bladder 240. For example, if the stored pressure/volume of fluid from position two is greater than or equal to what is required to inflate the low pressure balloon, the manifold 212 may simply be directed from position three to position four, and the balloon 22b attached to the low pressure inflation lumen may automatically inflate to the correct volume/pressure.

Turning to FIGS. 5A-5D, another embodiment of an inflation device 310 is shown that generally includes a manifold 212, source of inflation media 120, and a pressure relief valve 330 communicating via tubing 216, e.g., similar to previous embodiments. Unlike the previous embodiment, however, the pressure relief valve 330 includes a rigid casing or housing 332 with a balloon 340 mounted therein. The balloon 340 may include ends 340a, 340b attached to or otherwise sealingly connected to the tubing 216b, 216c such that inflation media from the syringe 120 passing through the tubing 216b, 216c also passes through the interior of the balloon 340. The balloon 340 may be formed from compliant or non-compliant material, e.g., having a nominal diameter substantially the same as the inner diameter of the casing 332.

When the balloon 340 is exposed to pressure above a predetermined threshold, e.g., when switching from position three (FIG. 5C) to position four (FIG. 5D), the pressure relief valve 330 may prevent excessive pressure from being applied to the low pressure inflation lumen/balloon, as all of the pressure/volume stored from position two may be used to inflate the balloon 340 inside the casing 332. Once the balloon 340 in the casing 332 has been inflated, the inflation device 330 may be used to apply a target pressure and/or volume desired for the low pressure inflation lumen.

Figure 6A:
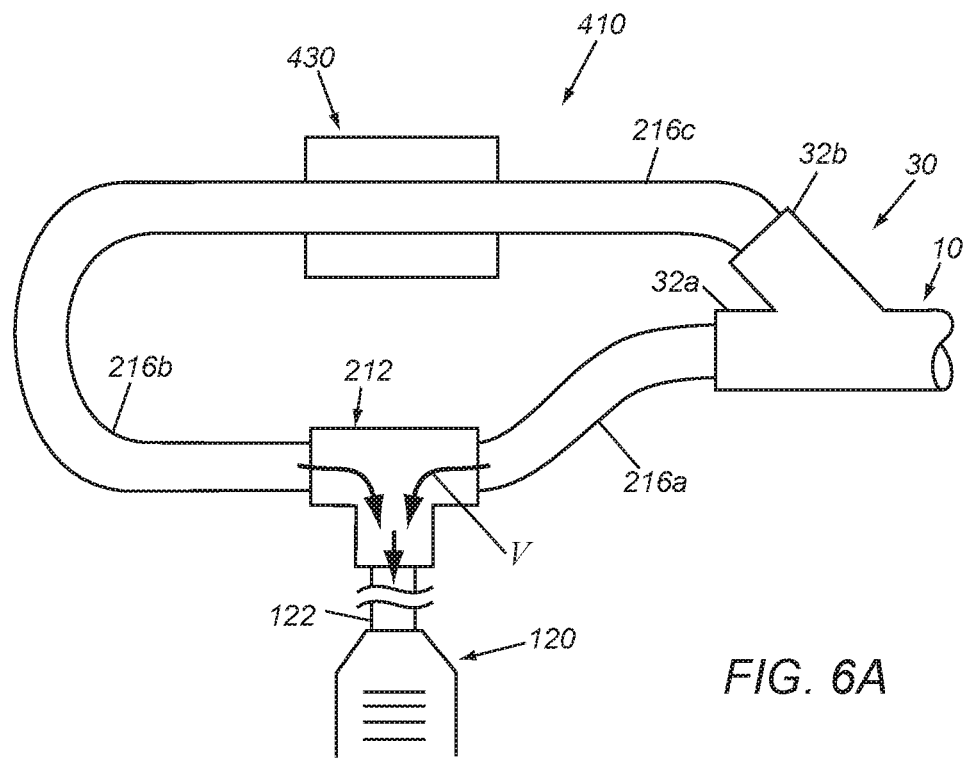
FIGS. 6A-6D are schematics showing still another exemplary embodiment of an inflation device including a pressure relief device.
Figure 6B:
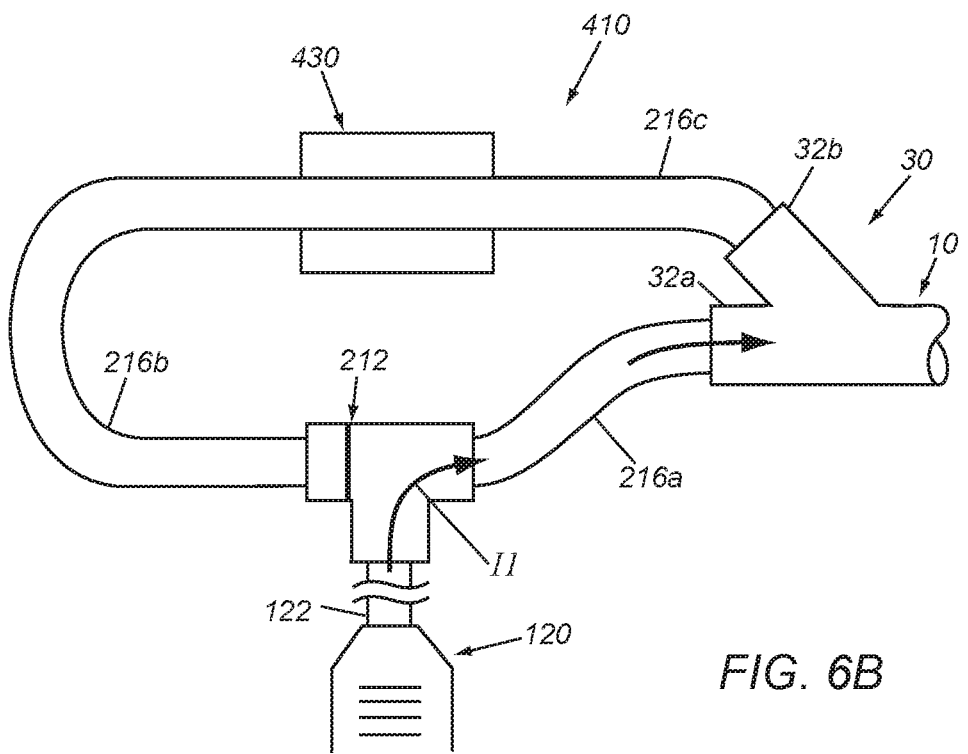
Figure 6C:
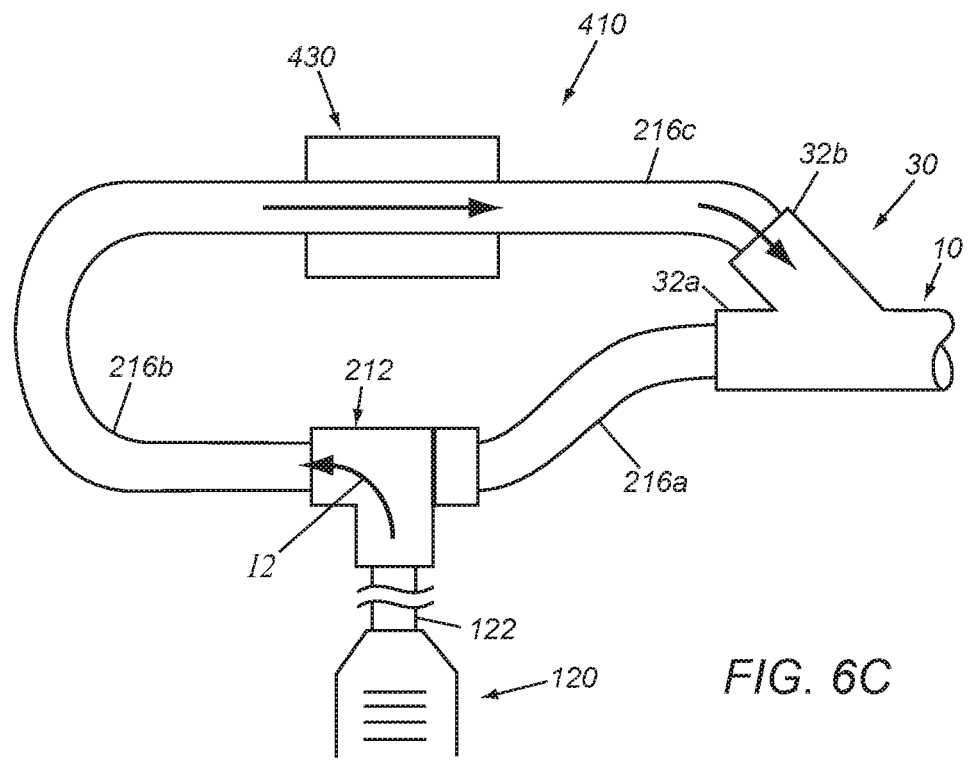
Figure 6D:
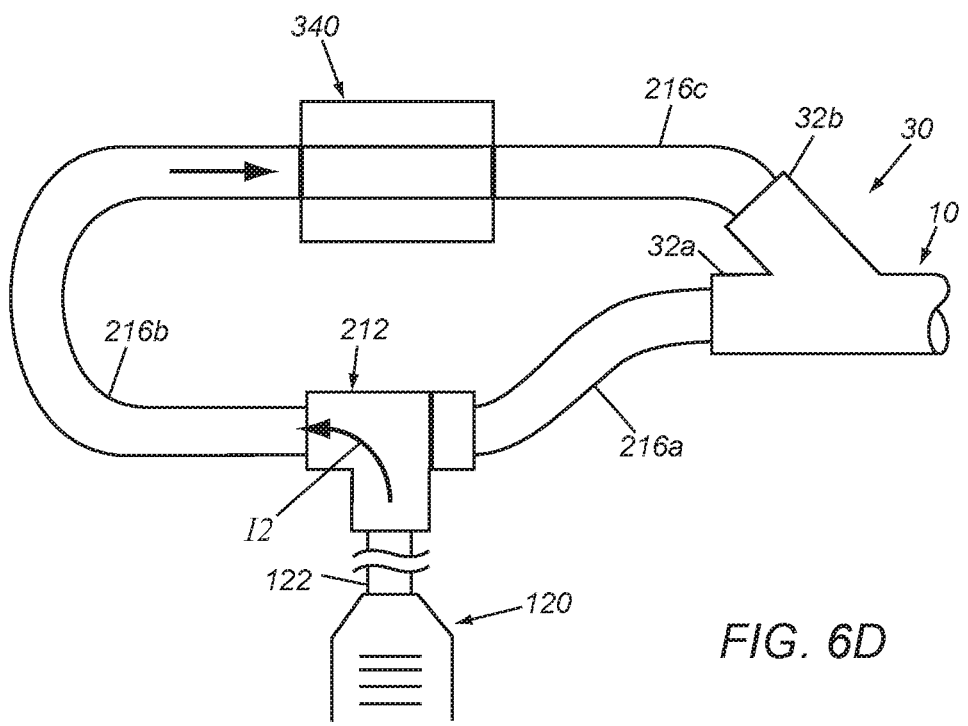

Turning to FIGS. 6A-6D, yet another embodiment of an inflation device 410 is shown that generally includes a manifold 212, source of inflation media 120, and a pressure relief device 430 communicating via tubing 216, e.g., similar to previous embodiments. Unlike the previous embodiments, the pressure relief device 430 includes a mechanism for restricting flow through tubing 216b, 216c, e.g., when the manifold 212 is directed from position three (FIG. 6C) and position four (FIG. 6D). The pressure relief device 430 may include an external clamp, e.g., positioned around a region of the tubing 216b, 216c, with an integrated pressure sensor and/or timer, that automatically stops flow when a predetermined pressure limit is exceeded and restores flow when the pressure drops below the predetermined pressure, thereby preventing undesired over-inflation of the balloon attached to the low pressure inflation lumen.

Alternatively, the pressure relief device 430 may include a manual flow arrest mechanism that may be activated manually by a user at any time. The pressure sensor/timer and associated clamping mechanism may be include known mechanical components (e.g., spring/diaphragm mechanisms) or electronically controlled components. In another alternative, the pressure relief device 430 may include an in-line mechanical flow restrictor, e.g., similar to the flow restrictor described elsewhere herein that may cause the balloon attached to the low pressure inflation lumen to slowly inflate, e.g., at a predetermined maximum rate, as the stored pressure pushes fluid through the flow restrictor. In yet another alternative, the pressure relief device 430 may include a one-way valve, optionally, including a flow restrictor or a manual device, e.g., a stopcock or other actuator, that may be manipulated to limit flow in a desired manner.

In these embodiments, with the manifold 212 in the second position shown in FIG. 6B, the syringe 120 may be used to deliver inflation media at a relatively high pressure, e.g., to inflate a inelastic and/or high pressure balloon, such as those described elsewhere herein. When the manifold is directed to the third and/or fourth positions, the pressure relief device 430 may prevent an residual pressure from being transmitted quickly to the second balloon, e.g., an elastic and/or low pressure balloon. The flow restrictor may slow fluid flow, thereby minimizing the risk of the second balloon being over-inflated and/or rupturing, while allowing the residual back pressure to continue to inflate the second balloon, e.g., until the pressure is released and/or vacuum is delivered to the inflation device 410.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An inflation device for selectively inflating and deflating first and second balloons on a tubular member via first and second lumens when the inflation device is coupled to the tubular member, the inflation device comprising:
- a first valve comprising a plurality of first valve ports and a first valve member movable between multiple positions for opening and closing fluid paths between the first valve ports;
- a second valve comprising a plurality of second valve ports and a second valve member movable between multiple positions for opening and closing fluid paths between the second valve ports; and
- an actuator coupled to the first and second valve members for simultaneously directing the first and second valve members sequentially between first, second, third, and fourth positions, wherein:
  - i) with the first and second valve members in the first position, a fluid path is provided from a source of inflation media coupled to one of the first valve ports to the first and second lumens such that, the source of inflation media may be actuated to pull a vacuum along the fluid path to collapse the first and second balloons simultaneously;
  - ii) with the first and second valve members in the second position, the second lumen is isolated while a fluid path between the first lumen and the source of inflation media is open such that inflation media delivered from the source of inflation media through the first lumen inflates the first balloon;
  - iii) with the first and second valve members in the third position, the first lumen is isolated for maintaining the first balloon inflated; and
  - iv) with the first and second valve members in the fourth position, a fluid path from the source of inflation media to the second lumen is open while the first lumen remains isolated such that inflation media delivered from the source of inflation media through the second lumen inflates the second balloon.

2. The inflation device of claim 1, wherein the actuator is coupled directly to the first valve member and wherein the second valve member is coupled to the first valve member such that actuation of the actuator causes the first valve member to rotate, thereby causing the second valve member to rotate.

3. The inflation device of claim 1, wherein the first and second valve members are coupled together by gears such that rotation of the first valve member in a clockwise direction causes the second valve member to rotate in a counterclockwise direction.

4. The inflation device of claim 1, wherein the actuator is rotatable in a first direction to direct the first and second valve members sequentially between the first, second, third, and fourth positions.

5. The inflation device of claim 4, wherein further rotation of the actuator in the first direction from the fourth position returns the first and second valve members to the first position.

6. The inflation device of claim 1, further comprising a flow restrictor in the fluid path when the first and second valve members are in the fourth position for limiting a rate of inflation of the second balloon.

7. The inflation device of claim 1, further comprising a pressure relief device in the fluid path communicating from the source of inflation media to the second lumen, the pressure relief device configured to release excess pressure when the first and second valve members are directed to the fourth position.

8. The inflation device of claim 7, wherein the pressure relief device comprises:
- a rigid casing comprising an interior communicating with the fluid path communicating from the source of inflation media to the second lumen and one or more holes in a sidewall thereof; and
- a flexible member at least partially around the casing comprising an interior communicating with the interior of the casing via the one or more holes,
- wherein the flexible member is configured to expand away from the casing when pressure from inflation media within the casing interior exceeds a predetermined pressure to limit one or both of flow and pressure from the inflation media communicating with the second balloon.

9. The inflation device of claim 8, wherein the flexible member is biased to collapse to maintain a target pressure within the fluid path to the second balloon.

10. The inflation device of claim 7, wherein the pressure relief device comprises:
- a rigid casing comprising an interior; and
- a flexible member within the casing interior and comprising ends communicating with the fluid path communicating from the source of inflation media to the second lumen such that inflation media traveling along the fluid path passes through an interior of the flexible member,
- wherein the flexible member is configured to expand within the casing interior when pressure from inflation media within the flexible member exceeds a predetermined pressure to limit one or both of flow and pressure from the inflation media communicating with the second balloon.

11. The apparatus of claim 1, wherein the actuator is configured to be actuated manually in a first direction to direct the first and second valve members sequentially from the first position to second, third, and fourth positions, and eventually back to the first position.

12. An apparatus for performing a medical procedure, comprising:
- a) a catheter comprising:
  - i) an elongate tubular member comprising a proximal end and a distal end sized for introduction into a patient's body;
  - ii) a first balloon on the distal end comprising a first interior communicating with a first lumen within the tubular member extending to a first lumen port on the proximal end; and
  - iii) a second balloon on the distal end comprising a second interior communicating with a second lumen within the tubular member extending to a second lumen port on the proximal end; and
- b) an inflation device comprising:
  - i) a first valve comprising a first valve port communicating with the first lumen port, a second valve port communicating with a source of inflation media, a third valve port, and a first valve member movable between multiple positions for opening and closing fluid paths between the first, second, and third valve ports; and
  - ii) a second valve comprising a fourth valve port communicating with the first valve port, a fifth valve port communicating with the second lumen port, and a second valve member movable between multiple positions for opening and closing fluid paths between fourth and fifth valve ports; and
  - iii) an actuator coupled to the first and second valve members for simultaneously directing the first and second valve members sequentially between first, second, third, and fourth positions, wherein:

with the first and second valve members in the first position, a fluid path is provided from the source of inflation media to the first and second lumens such that, the source of inflation media may be actuated to pull a vacuum along the fluid path to collapse the first and second balloons simultaneously;

with the first and second valve members in the second position, the second lumen is isolated while a fluid path between the first lumen and the source of inflation media is open such that inflation media delivered from the source of inflation media through the first lumen inflates the first balloon;

with the first and second valve members in the third position, the first lumen is isolated maintaining the first balloon inflated; and with the first and second valve members in the fourth position, a fluid path from the source of inflation media to the second lumen is open while the first lumen remains isolated such that inflation media delivered from the source of inflation media through the second lumen inflates the second balloon.

13. The apparatus of claim 12, wherein the actuator is coupled directly to the first valve member and wherein the second valve member is coupled to the first valve member such that actuation of the actuator causes the first valve member to rotate, thereby causing the second valve member to rotate.

14. The apparatus of claim 12, wherein the first and second valve members are coupled together by gears such that rotation of the first valve member in a clockwise direction causes the second valve member to rotate in a counterclockwise direction.

15. The apparatus of claim 12, wherein the actuator is rotatable in a first direction to direct the first and second valve members sequentially between the first, second, third, and fourth positions.

16. The apparatus of claim 15, wherein further rotation of the actuator in the first direction from the fourth position returns the first and second valve members to the first position.

17. The apparatus of claim 12, further comprising a flow restrictor in the fluid path when the first and second valve members are in the fourth position for limiting a rate of inflation of the second balloon.

18. The apparatus of claim 17, wherein the second valve comprises a sixth valve port also communicating with the second lumen in parallel with the fifth valve port to bypass the flow restrictor when the first and second valve members are in the first position.

19. The apparatus of claim 12, further comprising a pressure relief device in the fluid path communicating from the source of inflation media to the second lumen, the pressure relief device configured to release excess pressure when the first and second valve members are directed to the fourth position.

20. The apparatus of claim 19, wherein the pressure relief device comprises:
a rigid casing comprising an interior communicating with the fluid path communicating from the source of inflation media to the second lumen and one or more holes in a sidewall thereof; and
a flexible member at least partially around the casing comprising an interior communicating with the interior of the casing via the one or more holes, wherein the flexible member is configured to expand away from the casing when pressure from inflation media within the casing interior exceeds a predetermined pressure to limit one or both of flow and pressure from the inflation media communicating with the second balloon.

21. A method for selectively inflating and deflating first and second balloons on a tubular member via first and second lumens, the method comprising:
providing an inflation device comprising:
i) a first valve comprising a first valve port communicating with the first lumen, a second valve port communicating with a source of inflation media, a third valve port, and a first valve member movable between multiple positions for opening and closing fluid paths between two of the first, second, and third valve ports;
ii) a second valve comprising a fourth valve port communicating with the first valve port, and a fifth valve port communicating with the second lumen, and a second valve member movable between multiple positions for opening and closing fluid paths between fourth and fifth valve ports;
iii) an actuator on a handle or a hub coupled to the first and second valve members for simultaneously directing the first and second valve members sequentially between first, second, third, and fourth positions, wherein:
with the first and second valve members in the first position providing a fluid path from the source of inflation media to the first and second lumens, actuating the source of inflation media to pull a vacuum along the fluid path to collapse the first and second balloons simultaneously;
directing the first and second valve members to the second position isolating the second lumen while a fluid path between the first lumen and the source of inflation media is open;
with the first and second valve members in the second position, delivering inflation media from the source of inflation media through the first lumen to inflate the first balloon;
directing the first and second valve members to the third position isolating the first lumen, thereby maintaining the first balloon inflated;
directing the first and second valve members to the fourth position opening a fluid path from the source of inflation media to the second lumen while the first lumen remains isolated; and
with the first and second valve members in the fourth position, delivering inflation media from the source of inflation media through the second lumen to inflate the second balloon.

22. The method of claim 21, further comprising:
directing the first and second valve members to the first position to open a fluid path from the source of inflation media to the first and second lumens; and
actuating the source of inflation media to pull a vacuum along the fluid path to collapse the first and second balloons simultaneously.

23. The method of claim 21, wherein providing an inflation device comprises:
coupling the first valve port with a first lumen port on a proximal end of the tubular member such that the first valve port communicates with the first lumen; and coupling the second valve port with a second lumen port on a proximal end of the tubular member such that the second valve port communicates with the second lumen.

24. The method of claim 21, further comprising:
introducing a distal end of the tubular member carrying the first and second balloons in collapsed configurations into a patient's body, and
wherein the first and second valve members are directed to the second position when the distal end is positioned at a target location within the patient's body, and inflation media is delivered to inflate the first balloon at the target location.

25. The method of claim 24, wherein the first and second valve members are directed to the fourth position and inflation media is delivered to inflate the second balloon at the target location.

26. The method of claim 21, wherein the actuator is actuated manually in a first direction to direct the first and second valve members sequentially from the first position to second, third, and fourth positions, and eventually back to the first position.

\* \* \* \* \*